US009844459B2

United States Patent
Badawi

(10) Patent No.: US 9,844,459 B2
(45) Date of Patent: *Dec. 19, 2017

(54) DRY EYE TREATMENT SYSTEMS

(71) Applicant: Sight Sciences, Inc., Menlo Park, CA (US)

(72) Inventor: Paul Badawi, Menlo Park, CA (US)

(73) Assignee: Sight Sciences, Inc., Menlo Park, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 15/364,070

(22) Filed: Nov. 29, 2016

(65) Prior Publication Data

US 2017/0079834 A1    Mar. 23, 2017

Related U.S. Application Data

(63) Continuation of application No. 13/645,985, filed on Oct. 5, 2012, now Pat. No. 9,510,972, which is a
(Continued)

(51) Int. Cl.
*A61M 35/00* (2006.01)
*A61F 7/00* (2006.01)
*A61M 37/00* (2006.01)

(52) U.S. Cl.
CPC ............. *A61F 7/007* (2013.01); *A61M 35/00* (2013.01); *A61M 37/00* (2013.01);
(Continued)

(58) Field of Classification Search
CPC ...... A61F 2007/0004; A61F 2007/0071; A61F 2007/0075; A61F 2007/0072;
(Continued)

(56) References Cited

U.S. PATENT DOCUMENTS 2,108,934 A    2/1938 Albright
3,075,527 A    1/1963 Bechtold
(Continued)

FOREIGN PATENT DOCUMENTS

JP    2003-093431    4/2003
JP    2007-185017    7/2007
(Continued)

OTHER PUBLICATIONS

U.S. Appl. No. 14/967,116, filed Dec. 11, 2015.
U.S. Appl. No. 13/645,985, filed Oct. 5, 2012.
U.S. Appl. No. 13/343,407, filed Jan. 4, 2012.

*Primary Examiner* — Tatyana Zalukaeva
*Assistant Examiner* — Ariana Zimbouski
(74) *Attorney, Agent, or Firm* — Levine Bagade Han LLP

(57) ABSTRACT

Dry eye treatment apparatus and methods are described herein which generally comprise a patch or strip affixed to the skin of the upper and/or lower eyelids to deliver heat or other forms of energy, pressure, drugs, moisture, etc. (alone or in combination) to the one or more meibomian glands contained within the underlying skin. The treatment strip or strips include one or more strips configured to adhere to an underlying region of skin in proximity to one or both eyes of a subject such that the one or more strips allow for the subject to blink naturally without restriction from the one or more patches. Moreover, the one or more strips may be configured to emit energy to the underlying region of skin and where the one or more strips are shaped to follow a location of one or more meibomiam glands contained within the underlying region of skin.

36 Claims, 21 Drawing Sheets

Related U.S. Application Data continuation-in-part of application No. 13/343,407, filed on Jan. 4, 2012.

(52) U.S. Cl.
CPC .............. *A61F 2007/0004* (2013.01); *A61F 2007/0078* (2013.01); *A61F 2007/0086* (2013.01); *A61F 2007/0093* (2013.01); *A61F 2007/0095* (2013.01); *A61M 2037/0007* (2013.01); *A61M 2205/18* (2013.01)

(58) Field of Classification Search
CPC ........ A61F 2007/0076; A61F 2007/007; A61F 7/007; A61F 7/002; A61F 9/0008; A61F 13/124; A45D 44/02; A61K 8/0208
See application file for complete search history.

(56) References Cited

U.S. PATENT DOCUMENTS

| | | | |
|---|---|---|---|
| 3,173,419 A | 3/1965 | Dublier et al. | |
| 4,261,364 A | 4/1981 | Haddad et al. | |
| 4,325,254 A | 4/1982 | Svacina et al. | |
| 4,867,146 A | 9/1989 | Krupnick et al. | |
| 4,930,317 A | 6/1990 | Klein | |
| 4,962,761 A | 10/1990 | Golden | |
| 5,097,829 A | 3/1992 | Quisenberry | |
| 5,164,987 A | 11/1992 | Raven | |
| 5,643,336 A | 7/1997 | Lopez-Claros | |
| 6,066,164 A | 5/2000 | Macher et al. | |
| 6,074,414 A | 6/2000 | Haas et al. | |
| 6,155,995 A | 12/2000 | Lin | |
| D441,081 S | 4/2001 | Mueller | |
| 6,238,427 B1 | 5/2001 | Matta | |
| 6,416,534 B1 | 7/2002 | Montagnino et al. | |
| 6,511,446 B1 | 1/2003 | Wu | |
| 6,908,195 B2 * | 6/2005 | Fuller .................... | A61H 35/02 351/158 |
| D507,054 S | 7/2005 | Mueller et al. | |
| D507,055 S | 7/2005 | Mueller et al. | |
| D507,350 S | 7/2005 | Mueller et al. | |
| D507,651 S | 7/2005 | Mueller et al. | |
| 6,923,988 B2 | 8/2005 | Patel et al. | |
| D511,573 S | 11/2005 | Mueller et al. | |
| D513,323 S | 12/2005 | Mueller et al. | |
| 7,211,070 B2 | 5/2007 | Soroudi | |
| D613,408 S | 4/2010 | Gausmann et al. | |
| D614,303 S | 4/2010 | Gausmann et al. | |
| D614,774 S | 4/2010 | Gausmann et al. | |
| D617,443 S | 6/2010 | Grenon et al. | |
| 7,758,190 B2 | 7/2010 | Korb et al. | |
| 7,833,205 B2 | 11/2010 | Grenon et al. | |
| D638,128 S | 5/2011 | Prokop et al. | |
| 7,976,573 B2 | 7/2011 | Korb et al. | |
| 7,981,095 B2 | 7/2011 | Grenon et al. | |
| 7,981,145 B2 | 7/2011 | Korb et al. | |
| 7,981,146 B2 | 7/2011 | Korb et al. | |
| 7,981,147 B2 | 7/2011 | Korb et al. | |
| 7,988,294 B2 | 8/2011 | Korb et al. | |
| 8,007,524 B2 | 8/2011 | Korb et al. | |
| 8,025,689 B2 | 9/2011 | Korb et al. | |
| 8,506,539 B2 | 8/2013 | Guillon et al. | |
| 8,535,363 B1 | 9/2013 | Lewis | |
| 9,510,972 B2 | 12/2016 | Badawi | |
| 2002/0117495 A1 | 8/2002 | Kochman et al. | |
| 2003/0167556 A1* | 9/2003 | Kelley ................. | A45D 44/002 2/206 |
| 2004/0116990 A1 | 6/2004 | Agarwal et al. | |
| 2005/0119629 A1 | 6/2005 | Soroudi | |
| 2005/0187502 A1 | 8/2005 | Krempel et al. | |
| 2006/0018953 A1 | 1/2006 | Guillon et al. | |
| 2006/0069420 A1 | 3/2006 | Rademacher et al. | |
| 2006/0154642 A1 | 7/2006 | Scannell | |
| 2006/0200052 A1 | 9/2006 | Lin | |
| 2006/0235497 A1 | 10/2006 | Zanotti | |
| 2007/0016255 A1 | 1/2007 | Korb et al. | |
| 2007/0060988 A1 | 3/2007 | Grenon et al. | |
| 2008/0039749 A1 | 2/2008 | Kopanic et al. | |
| 2008/0081999 A1 | 4/2008 | Gravely et al. | |
| 2008/0109053 A1 | 5/2008 | Grenon et al. | |
| 2008/0114423 A1 | 5/2008 | Grenon et al. | |
| 2008/0114424 A1 | 5/2008 | Grenon et al. | |
| 2008/0132987 A1 | 6/2008 | Westlund et al. | |
| 2009/0020521 A1 | 1/2009 | Blaszczykiewicz et al. | |
| 2009/0048590 A1 | 2/2009 | Conrad et al. | |
| 2009/0137533 A1 | 5/2009 | Adkins, Jr. | |
| 2009/0149925 A1 | 6/2009 | MacDonald et al. | |
| 2009/0312823 A1 | 12/2009 | Patience et al. | |
| 2010/0010598 A1 | 1/2010 | Igaki et al. | |
| 2010/0114086 A1 | 5/2010 | Deem et al. | |
| 2010/0174501 A1 | 7/2010 | Myadam | |
| 2010/0267751 A1 | 10/2010 | Beals et al. | |
| 2011/0046581 A1 | 2/2011 | Linder | |
| 2011/0081333 A1* | 4/2011 | Shantha ................. | A61N 1/328 424/94.62 |
| 2011/0275410 A1 | 11/2011 | Caffey et al. | |
| 2012/0062840 A1 | 3/2012 | Ballou et al. | |
| 2012/0191164 A1 | 7/2012 | Gander et al. | |
| 2012/0213840 A1 | 8/2012 | Lim | |
| 2013/0172790 A1 | 7/2013 | Badawi | |
| 2013/0172829 A1 | 7/2013 | Badawi | |
| 2013/0281893 A1 | 10/2013 | Yang | |
| 2016/0106576 A1 | 4/2016 | Badawi et al. | |

FOREIGN PATENT DOCUMENTS

| | | |
|---|---|---|
| JP | 2011-188958 | 9/2011 |
| WO | WO 99/20213 | 4/1999 |
| WO | WO 00/69506 | 11/2000 |
| WO | WO 02/067688 | 9/2002 |
| WO | WO 2004/006801 | 11/2004 |
| WO | WO 2006/099413 | 9/2006 |
| WO | WO 2008/085162 | 7/2008 |
| WO | WO 2008/100647 | 8/2008 |
| WO | WO 2013/103413 | 7/2013 |

\* cited by examiner

DRY EYE TREATMENT SYSTEMS

CROSS-REFERENCE TO RELATED APPLICATIONS

This is a continuation of U.S. patent application Ser. No. 13/645,985 filed Oct. 5, 2012 (now U.S. Pat. No. 9,510,972), which is a continuation-in-part of U.S. patent application Ser. No. 13/343,407 filed Jan. 4, 2012, each of which is incorporated herein by reference in its entirety.

FIELD OF THE INVENTION

The present invention relates to methods and apparatus for treatment of dry eye syndrome and other related conditions. More particularly, the present invention relates to methods and apparatus for the treatment of dry eye syndrome using adhesive strips which are specifically contoured or shaped to adhere to selected regions around a patient's eyes or peri-orbital region.

BACKGROUND OF THE INVENTION

Tears are a complex mixture of water, lipids, mucus, proteins and electrolytes and this mixture helps to maintain a smooth and clear optical surface and also helps to protect the eyes from infection. The tear film has three basic layers: oil, water, and mucus and problems or disturbances in any of these layers can cause dry eyes symptoms.

The outermost layer of the tear film is typically comprised of an oil layer containing fatty acids and lipids (meibum) which are produced primarily by sebaceous glands called the meibomian glands located along the eyelid margin. The oil layer smoothes the tear surface and slows evaporation of the watery middle layer. However, if the meibomian glands fail to produce enough oil, produce suboptimal fatty acid mixtures, or if the glands become obstructed or clogged, the watery layer typically evaporates too quickly causing dry eyes. A blockage of the meibomian glands can lead to enlarged glands or infections. Dry eyes are thus common in people whose meibomian glands are obstructed or functioning improperly.

The middle layer of tears is composed primarily of an aqueous solution, which is produced by the lacrimal glands (tear glands). The middle layer cleanses the eyes and washes away foreign particles or irritants, maintains a clear optical medium, and keeps the ocular surface moist. The innermost layer of the tear film is composed primarily of mucus which helps to spread the tears evenly over the surface of the eyes. A lack of mucus in the tear film is also associated with dry eye syndrome.

As discussed above, the meibomian glands are oil-secreting glands located within both the upper and lower eyelids. There are approximately 30 to 40 glands along the upper eyelid and approximately 20 to 30 glands along the lower eyelid with the ducts for each of the glands opening along the inner edge of the free margin of the respective lids by minute foramina through which their secretion is released to prevent the lids adhering to each other. An example of the location of the meibomian glands is illustrated in the cross-sectional view of the upper eyelid UL shown in FIG. 1A which illustrates the relative positioning of a single meibomian gland MG. Other glands and anatomical features are illustrated for reference, e.g., the glands of Wolfring GW, tarsus TR, gland of Moll GM, gland of Zeis GZ, gland of Krause GK, upper fornix UF, conjunctiva CN and cornea CR of the eye which is partially covered by the upper eyelid UL.

As illustrated, the meibomian gland MG is positioned along a length of the upper eyelid UL (and lower eyelid LL) with the duct opening along the inner edge of the eyelid UL in proximity to a surface of the underlying eye.

FIG. 1B illustrates a front view of a patient's eye having the upper eyelid UL and lower eyelid LL in a closed position, such as when the patient blinks. As shown, the meibomian glands MG may be seen aligned adjacent to one another over both the upper UL and lower eyelids LL. FIG. 1C also shows a perspective view of a patient's eye in the open position to illustrate how the meibomian glands are typically aligned relative to one another when the patient's eye is opened.

Blinking is thought to be the primary mechanism to open the orifice of the meibomian glands to allow for the release of oil secretions from the glands. The natural blinking motion and blinking force causes the upper lid to pull a sheet of the lipids secreted by the meibomian glands over the two underlying layers of the tear film thus forming the protective coating which limits the rate at which the underlying layers evaporate. It is estimated that approximately 65% of meibomian gland disease or dry eye results from a defective lipid layer or an insufficient quantity of such lipids that results in accelerated evaporation of the aqueous layer. Hence, blinking disorders, or other disorders that affect proper tear distribution, may also cause or exacerbate meibomian gland dysfunction or dry eye.

As the eyelids close in a total blink, the superior and inferior fornices, which hold a reservoir of tears, are compressed by the force of the preseptal muscles and the eyelids move toward one another. The upper eyelid, for instance, moves over the eye while exerting upon the eye surface a force which helps to clear the front of the eye of debris, insoluble mucin, and also expresses the oil secretions from the meibomian glands. The lower lid moves horizontally in the nasal direction and pushes debris toward both punctae, the openings that ultimately drain into the nasal cavities.

As the eyelids open the tear film is redistributed where the upper lid pulls the aqueous phase via capillary action and the lipid layer spreads as quickly as the eyelids move. Hence, eyelid movement is accordingly important in tear-film renewal, distribution, turnover, and drainage.

For a variety of reasons, the meibomian glands can become blocked, plugged, or occluded resulting in meibomian gland dysfunction and dry eye disease. The obstruction that triggers the disease can occur anywhere within the meibomian gland, for instance, at the gland's surface or orifice preventing normal lipid secretions from flowing; in the main channel of the gland which may be narrowed or blocked; or in other locations deeper within the gland that lead to the main channel.

Treatments for blocked meibomian glands may include a number of conventional treatments. One course of treatment includes the application of soap and cleaning agents, eyelid scrubs, or antibiotics to reduce eyelid inflammation. Antibiotics such as tetracycline, doxycycline, metronidazole, or erythromycin can be administered orally or topically to help regulate or improve meibomian gland lipid production. Inflammation on the surface of the eye may also be controlled with topical drugs such as corticosteroids or cyclosporine (RESTASIS®, Allergan, Inc., CA), or other anti-inflammatory compounds or immune-suppressants. Evidence suggests that ocular surface inflammation is not only associated with meibomian gland dysfunction but also with dry eye syndrome.

Other examples of dry eye treatments may include the application of prescription eye inserts for people with moderate to severe dry eyes symptoms who are unable to use artificial tears. An eye insert, e.g., hydroxypropyl cellulose (LACRISERT®, Merck & Co., Inc., NJ), may be inserted between the lower eyelid and eye. The insert dissolves slowly to release a substance which lubricates the eye. Alternatively, special contact lenses may be used to shield the surface of the eye to trap moisture.

In other treatments, the patient's tear ducts may be closed to prevent the tear film from draining away from the surface of the eye too quickly by procedures such as insertion of punctal plugs into the tear ducts or cauterizing the tissues of the drainage area. Aside from implants or cauterizing treatments, dry eye syndrome may be treated using pharmaceutical agents such as eyedrops, ointments which coat the eyes, etc. Artificial tears, gels, ointments, autologous serum tears, or albumin drops have all been employed in the treatment of dry eye.

Additionally, warm compresses are also typically placed over the eyes and are used to restore function to the meibomian glands by melting any lipid plugs as well as incorporating massaging of the lids which may further express meibomian gland contents. However, application of warm compresses require their application two to three times daily during which time patients may incorrectly target only one of the affected lids and are also prevented from seeing out of the treated eye because of the compresses. Compresses may be too hot, further exacerbating inflammation, or they may cool too quickly preventing adequate therapeutic effect.

Other treatment devices have also been developed which cover the entire affected eye to apply heat and a massaging force directly to the affected eyelids. However, such devices, like the compresses, require that the patient's eyes be temporarily but completely obstructed during the treatment resulting in discomfort, lost productivity, and potentially lower compliance among patients. Additionally, these treatments require visits to a physician or healthcare provider and are not as well-suited for widespread consumer adoption.

Accordingly, there exists a need for methods and apparatus which are relatively simple to routinely use for the patient, which also allow for the patient to continue their normal activities, is non-obtrusive and non-disruptive, and which also take advantage of the patient's natural physiological activities to facilitate treatment.

SUMMARY OF THE INVENTION

In treating conditions such as meibomian gland dysfunction or dry eye syndrome, a patch or strip can be affixed to the skin of the upper and/or lower eyelids to deliver heat or other forms of energy, pressure, drugs, moisture, etc. (alone or in combination) to the one or more meibomian glands contained within the underlying skin. In particular, the assembly for the treatment strip or strips may generally comprise one or more strips configured to adhere to an underlying region of skin in proximity to one or both eyes of a subject such that the one or more strips allow for the subject to blink naturally without restriction from the one or more patches. Moreover, the one or more strips may be configured to emit energy to the underlying region of skin and where the one or more strips are shaped to follow a location of one or more meibomian glands contained within the underlying region of skin.

In use, the one or more strips may be adhered to a region of skin in proximity to one or both eyes of a subject such that the one or more strips allow for the subject to blink naturally without restriction from the one or more patches. While adhered, the strips may emit energy to the region of skin, where the one or more strips are shaped to follow a location of one or more meibomian glands contained within the region of skin. Alternatively, while the strip may not directly overly a meibomian or other ocular or orbital gland, it may deliver energy or absorb energy from underlying neighboring vasculature which ultimately supplies said glands. In other words, heating or cooling the blood supply to the eyelids, meibomian glands, and/or lacrimal glands using these strips may affect their function and metabolism while not necessarily needing to directly overly them in particular variations.

The upper strip may thus have an upper curved or arcuate periphery which is shaped to extend and follow the upper (or superior) border of the meibomian glands (such as along or up to the upper eyelid crease) while the straightened periphery of the lower edge may be shaped to extend and follow the lower (or inferior) border of the meibomian glands such as along the free margin of the upper eyelid. Although straightened, the lower edge may be gently curved or arcuate in alternative variations. The lower strip may similarly have an upper straightened periphery to extend and follow the upper (or superior) border of the meibomian glands along the free margin of the lower eyelid and a lower curved or arcuate periphery to extend and follow the lower (or inferior) border of the meibomian glands along the lower eyelid (such as along or up to the lower eyelid crease). Alternatively, the upper periphery of the lower strip may also be gently curved or arcuate in alternative variations as well.

In other words, with the tarsal plate containing the meibomian glands which span from proximal to distal, the peripheral edges of the treatment strips may correspond to the distal eyelid margin and proximal peripheral edge and the treatment strips can assume multiple configurations. Generally, the peripheral distal edge of the treatment strip may be relatively straight or assume a gentle curve either of which can follow the underlying distal eyelid margin and tarsal plate while having a proximal peripheral edge that is relatively curved to assume the more curved proximal edge of the underlying tarsal plate.

The strips may be used individually for placement upon only the upper eyelid or only the lower eyelid depending upon the desired treatment. Moreover, the lengths of the treatment strips may also be varied to target individual meibomian glands for providing a targeted treatment, if desired, and as described in further detail herein. Additionally, while the treatment strips may be sized generally, they may also be custom made or sized for a specific individual's eyelid dimensions.

Because of the specific contoured sizes and flexibility of the treatment strips the treatment strips may be placed upon the patient to apply therapy to the underlying meibomian glands allowing the patient's eyes to be opened and closed normally without interference from one or both treatment strips. Accordingly, the treatment strips contoured size, shape, and flexibility allow for treatment to occur while also allowing for the patient to have one or both eyes remain opened such that normal, physiologic blinking can proceed during the course of treatment. Rather than relying on an application of any type of external force, the treatment strips take advantage of the eye's natural mechanism for clearing oil from the meibomian glands via blinking. Hence, the treatment strips may be adhered in place for treatment without any further intervention by the patient or healthcare provider such that the treatment strips may apply, e.g., heat energy, to melt or liquefy any waxy or solid meibomian gland obstructions while the eyes remain unobstructed and are allowed to blink naturally. The treatment strips thus allow for the natural blinking force to clear the glands of the heat-treated softened obstructions before they have re-solidified unlike other treatments which require that the patient keep their eyes closed or obstructed during the course of a treatment and prevent or inhibit the patient from blinking.

The treatment strip may be configured to have a contact layer (e.g., fabricated from conductive materials such as metals, alloys, porous ceramics, engineering ceramics, woods, polymers, composites, foams, polymer foams, fabrics, elastomers, etc.) which may protect the skin from burns or any other adverse effects. A second heating layer may be positioned above the contact layer (or directly in contact against the skin) for generating the heat energy and an insulative layer may be positioned atop the heating layer for focusing, directing, or reflecting the heat towards the underlying skin surface as well as to protect the patient from contact with the heating layer from other parts of the body. The insulative layer may accordingly be fabricated from a variety of insulative materials, e.g., foams, foam tapes, gauze, silicone, microporous polyethylene films, fabrics, polymers, etc.

Although the application of heat energy from the treatment strips is described, other variations may alternatively include the application of using the treatment strips for cooling of the underlying skin. Rather than using the heating layer in an exothermic reaction, the layer may be configured to utilize an endothermic reaction instead to provide for cooling of the skin. Cooling, rather than heating, may be applied for conditions such as reducing inflammation, alleviating allergies or tired eyes, etc. particularly as the patient rests or sleeps.

Aside from the application of heat energy from the treatment strips, the strips may also include a layer for the diffusion or release of one or more pharmaceutical, biological, or chemical agents either alone or in combination with the heat treatment. For instance, the pharmaceutical, biological, or chemical agents may be incorporated into the either the contact layer, insulative layer, or in a separate layer entirely, for transdermal delivery to the meibomian glands or to the areas surrounding the meibomian glands for additional and/or alternative treatments. In the event that the pharmacological or chemical agent is released during the heat treatment, the heat may help to improve penetration of any drugs into the underlying skin.

While the treatment strips may incorporate various layers into the strips to effect various different treatments, the strips may also be varied in size, shape, contour, etc. depending upon the desired treatment areas so long as the treatment strips are contoured or shaped to follow the location of at least one meibomian gland.

While the treatment strips may be applied to one or more of the meibomian glands, variations of the strip may also be used to treat other glands such as the sebaceous glands, e.g., for acne treatment. Treatment strips used to treat acne may utilize different pharmacological treatments. Moreover, the treatment strips may be used to potentially treat eye disorders beyond meibomian gland dysfunction.

Yet another example may include use of the treatment strips for treating disorders of the lacrimal gland and/or palpebral lacrimal gland which are located above the eye. Variously sized treatment strips, such as lacrimal gland strips which are sized to have a curved upper periphery, may be sized for placement directly over the skin surface above where the lacrimal glands are located. The lacrimal glands and/or palpebral lacrimal gland may be treated alone or in combination with the treatment strips contoured for treatment of the meibomian glands.

While the treatment strips may be applied over the meibomian glands to apply the heat energy, the treatment does not require the application of any external force applied by the strip or any other external device but may utilize the natural blinking of the patient to facilitate treatment. However, in additional variations, the treatment strips may be configured to apply both the heat treatment as well as an external force. Any number of mechanisms may be utilized to apply a pinching or biasing force to provide for compression of the underlying skin and of the meibomian glands during application of the heat therapy.

Aside from a compression force, the strip may be formed with alternative components such as a mechanical component to impart vibrational energy or other forms of energy to facilitate the expression of the meibomian glands and promote oil secretion.

In yet another variation, one or both treatment strips may be configured to incorporate an indicator, e.g., LED light, alarm, vibration element, etc., electrically coupled to a power supply and/or processor to alert the patient when a prescribed treatment has been completed. This feature (and any of the other features) may be combined with any of the other variations of the treatment strips described herein as practicable.

With the incorporation of a processor into the treatment strips, treatment times or other parameters such as temperature of the strips may be programmed and optionally shut on or off selectively by the patient or automatically. Moreover, other parameters such as the frequency of the heat delivery or other stimulation may also be programmed by the processor to provide further flexibility in treatment.

DETAILED DESCRIPTION OF THE INVENTION

In treating conditions such as meibomian gland dysfunction (MGD), which is commonly associated with the evaporative form of dry eye syndrome (DES), a patch, strip or thin adhesive device can be affixed to the skin of the upper and/or lower eyelids to deliver heat or other forms of energy, pressure, drugs, moisture, etc. (alone or in combination) to the one or more meibomian glands contained within the underlying skin. In particular, the treatment strip or strips may be configured and sized specifically for placement over one or more targeted meibomian glands contained within the skin of the upper and/or lower eyelids. The application of thermal therapy, e.g., heating or cooling, can cross the eyelids quite easily as the eyelids are generally the thinnest skin found on the human body and the tissue is highly vascularized. With the root of the eyelid located proximally and the eyelid margin located distally, the net arterial flow of blood flows from proximal to distal. So wherever these treatment strips are placed, the heating or cooling therapy may easily be carried throughout the eyelid and any structures contained therein, e.g., meibomian glands MG, lacrimal glands LG, gland of Zeis GZ, gland of Moll GM, gland of Wolfring GW, gland of Kraus GK, etc.

Moreover, because the eyelid is so thin, the heating or cooling therapy can be transmitted to the ocular surface and the eye itself (described in further detail below). Thus, the therapy can impart energy to the conjunctiva, goblet cells, episcleral vasculature, cornea, aqueous humor, iris, ciliary body, and possibly the anterior vitreous and lens. Thus, any thermal therapy by the treatment strips may also impact and be used to treat ocular surface disorders and anterior segment diseases, e.g., conjunctivitis, keratitis, keratopathy, iritis, cyclitis, glaucoma, cataract, etc. Also, there may be use in the postoperative state-like after LASIK, PRK, or cataract or corneal surgery or other ocular, peri-ocular, intraocular, or eyelid surgery, as described in further detail below.

Figure 1A:
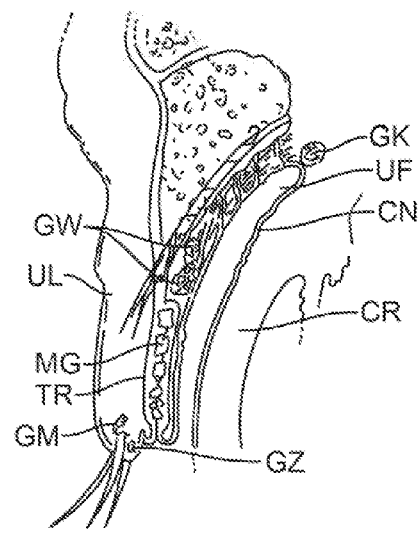
FIG. 1A shows a cross-sectional side view of an upper eyelid and an example of the location of a meibomian gland.
Figure 1B:
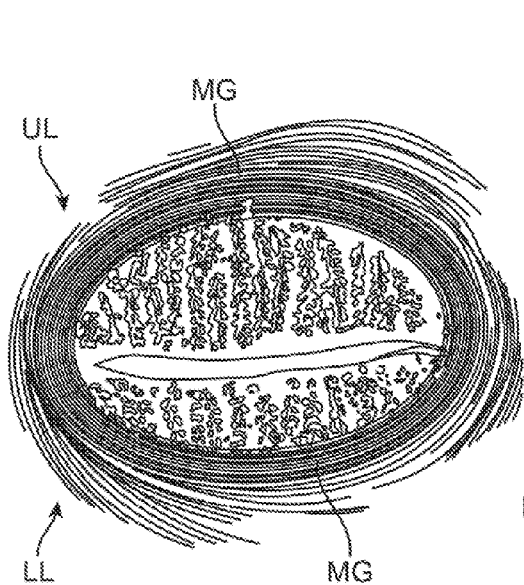
FIG. 1B shows a front view diagram of meibomian gland distribution in human eyelids having the upper eyelid and lower eyelid in a closed position, such as when the patient blinks, and the alignment of the meibomian glands over both the upper and lower eyelids.
Figure 1C:
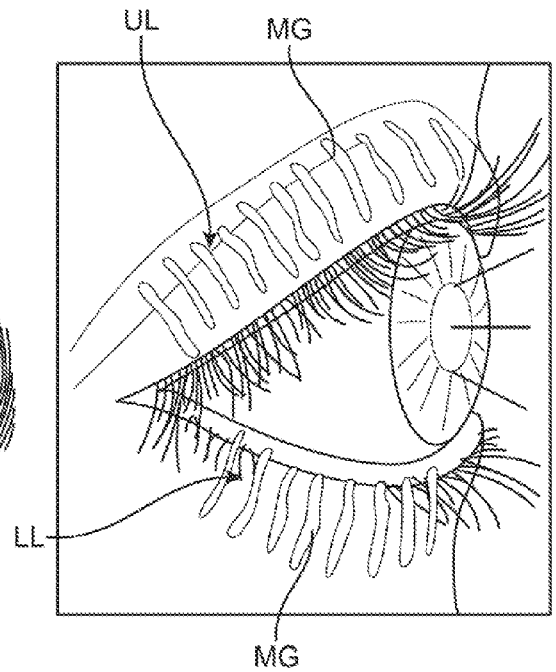
FIG. 1C shows a perspective view of a patient's eye in the open position to illustrate how the meibomian glands are typically aligned relative to one another when the patient's eye is opened.
Figure 2A:
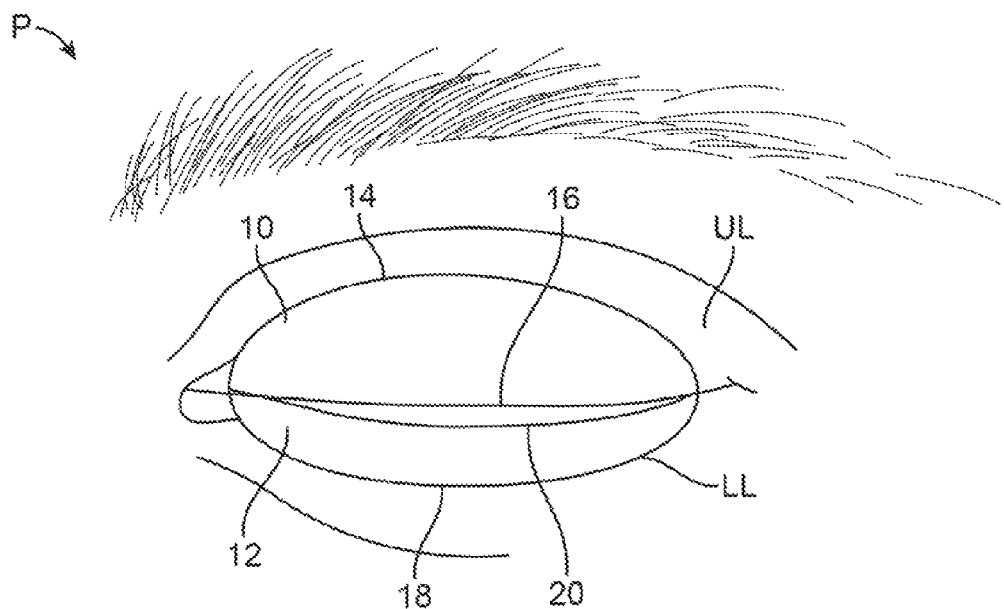
FIG. 2A shows a front view of a patient's eye in a closed position with an example of treatment strips which adhere onto the upper or lower eyelids (or both) and where the strips are sized or contoured for placement directly over the meibomian glands located in the underlying eyelids.

As shown in the front view of FIG. 2A, one variation of such treatment strips may be seen as being adhered temporarily upon the upper eyelid UL and lower eyelid LL over an eye of a patient P when closed for illustrative purposes. The contoured upper strip 10 may be sized for adherence directly upon the skin of the upper eyelid UL such that the strip 10 has a configuration and shape which follows the location of the one or more meibomian glands contained within the underlying skin of the upper eyelid UL. Likewise, the contoured lower strip 12 may also have a configuration and shape which follows the location of the one or more meibomian glands contained within the underlying skin of the lower eyelid LL. In other variations, the contoured strip may stop at the eyelid crease or cross over it as described in other variations below.

The upper strip 10 may thus have an upper curved or arcuate periphery 14 which is shaped to extend and follow the upper (or superior) border of the meibomian glands (such as along or up to the upper eyelid crease) while the straightened periphery 16 of the lower edge may be shaped to extend and follow the lower (or inferior) border of the meibomian glands such as along the free margin of the upper eyelid UL. The lower strip 12 may similarly have an upper straightened periphery 20 to extend and follow the upper (or superior) border of the meibomian glands along the free margin of the lower eyelid LL and a lower curved or arcuate periphery 18 to extend and follow the lower (or inferior) border of the meibomian glands along the lower eyelid LL (such as along or up to the lower eyelid crease). The use of the terms lower and upper herein refer to the periphery of the treatment strips when placed upon the patient P (human or animal) and are used herein for descriptive purposes.

While the treatment strips 10, 12 are both shown adhered upon the respective upper eyelid UL and lower eyelid LL, the strips 10, 12 may be used individually for placement upon only the upper eyelid UL or only the lower eyelid LL depending upon the desired treatment. Moreover, the lengths of the treatment strips 10, 12 may also be varied to target individual meibomian glands for providing a targeted treatment, if desired, and as described in further detail herein.

While the treatment strips 10, 12 are shown placed upon the closed eyelids of the patient P, the strips 10, 12 are arc-shaped or flexible enough to assume the curvature of the patient's eyelid margin and may be long enough to cover some or all of the underlying meibomian glands in the tarsal plate. While the treatment strips 10, 12 may be sized generally, they may also be custom made or sized for a specific individual's eyelid dimensions or shaped to optimize adhesion and/or comfort and/or stability. Generally, the treatment strips 10, 12 may have a length anywhere from about 1 mm to 50 mm depending upon the desired treatment length as well as the anatomical considerations of the patient since the typical palpebral fissure length in an adult is about 27 mm to 30 mm. Thus, to cover as many as all of the meibomian glands, the treatment strips 10, 12 may be sized to have length of, e.g., 25 mm to 30 mm, or if sized to cover just beyond all the meibomian glands, a length of, e.g., 30 mm to 50 mm (or more if needed to optimize adhesion/comfort/stability). Moreover, one or both treatment strips 10, 12 can have a width ranging anywhere from about 1 mm to 25 mm since the typical eyelid crease in a Caucasian male is about 8 mm to 9 mm above the eyelid margin while in Caucasian females it is about 9 mm to 11 mm above the eyelid margin (or more if needed for adhesion/comfort and potentially increased efficacy from heating or cooling the inbound blood flow). Customization enables it to fit any particular anatomy, race, ethnicity, etc. Moreover, the treatment strips may be manufactured with varying levels of flexibility to accommodate the ergonomics of the eyelid and eyelid blink for optimal comfort and minimal obtrusiveness or movement.

Figure 2B:
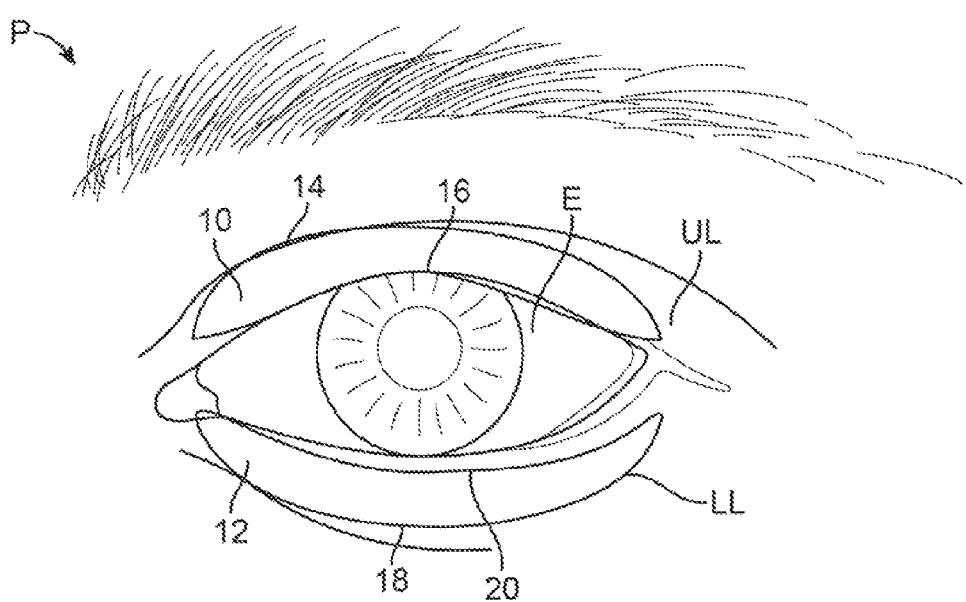
FIG. 2B shows the treatment strips of FIG. 2A illustrating how the strips may remain adhered to the patient skin while allowing for the eyelids to retract and allow for the patient to continue blinking while viewing normally out of the eye. While the strips may be applied from eyelid margin to eyelid crease, they may alternatively flex or accordion and/or compress during blinks to prevent impairment of normal blinking and maximize comfort.

Because of the specific contoured sizes and flexibility of the treatment strips 10, 12, the treatment strips may be placed upon the patient P by the patient himself/herself for consumer use or by a healthcare provider to apply therapy to the underlying meibomian glands allowing the patient's eyes to be opened and closed normally, as shown in FIG. 2B, without interference from one or both treatment strips. While the strips may be applied from eyelid margin to eyelid crease, they may alternatively flex or accordion and/or compress during blinks to prevent impairment of normal blinking and maximize comfort.

Typical treatment patches, such as for application of a warm compress, are generally sized for placement over the entire eye or eyes such that the patient is unable to open their eyes or blink during a treatment session. Yet, because of the strong association between DES and MGD (for instance, MGD includes the spectrum of MGD, meibomitis, blepharitis, and ocular rosacea), natural blinking by an individual is the mechanism by which meibomian gland secretions are normally released onto the eyelid margin and over the tear. In the absence of blinking, the oil contained within the meibomian glands remain unexpressed within the glands' terminal ducts and fail to contribute to distribution of the oily layer upon the tears.

Accordingly, the treatment strips 10, 12 contoured size, shape, and flexibility allow for treatment to occur while also allowing for the patient to have one or both eyes remain opened such that normal, physiologic blinking can proceed during the course of treatment. Rather than relying on an application of any type of external force to express the oil or obstruction from the glands, the treatment strips 10, 12 take advantage of the eye's natural mechanism for clearing oil from the meibomian glands via blinking. Hence, the treatment strips 10, 12 may be adhered in place for treatment without any further intervention by the patient or healthcare provider such that the treatment strips 10, 12 may apply, e.g., heat energy, to melt or liquefy any waxy or solid meibomian gland obstructions while the eyes remain unobstructed and are allowed to blink naturally. The treatment strips 10, 12 thus allow for the natural blinking to clear the glands of the heat-treated softened obstructions before they have re-solidified unlike other treatments which require that the patient keep their eyes closed or obstructed during the course of a treatment and prevent or inhibit the patient from blinking. Delivery of heat may also increase blood flow by promoting vasodilation as increased delivery of blood can affect metabolism, temperature of other tissues, may have effects on inflammation, and can thereby improve tissue function.

Because some patients have obstructions or occlusions in their meibomian glands that may not sufficiently melt, loosen, or soften without attaining heightened temperatures at the meibomian glands, the treatment strips 10, 12 may apply heat or other treatments to the surface of the eyelids for a significant period of time for relatively longer treatment times and at higher treatment temperatures because of the ability of the treatment strips 10, 12 to remain attached to the patient during any given period throughout the day. Patients can assume their daily activities with their eyes open and eyes blinking and with the comfort of a strip-based treatment. Moreover, patients can affix the treatment strips as many times as needed throughout the day, week, month, etc. until dry eye symptoms subside. This increases the frequency of treatment, convenience of treatment, and thus efficacy of treatment.

Because of the prolonged treatment times, the application of a separate force beyond the application of the strips may not be needed so long as the patient is able to continue blinking during the course of treatment. Moreover, the treatment frequency may be varied depending upon the severity of the condition to be treated. One example for potential treatment frequency may include application of one or both strips, e.g., up to six times per day for ten minutes or up to an hour or more for each treatment. Moreover, because the treatment strips are positioned over the meibomian glands which overlie the ocular surfaces, the application of the heating therapy may also indirectly heat the ocular surface as well and may further reduce any chronic ocular surface inflammation, chronic conjunctival inflammation, or corneal neovascularization.

Aside from heating of the ocular surface, heat therapy may also optionally be used to potentially provide for indirect heating through the ocular surface as well for heating of the retina to provide a thermal therapy to limit inflammation and neovascularization which are underlying conditions for diseases such as Wet age-related macular degeneration (AMD) and Diabetic Retinopathy.

While the treatment strips 10, 12 may be used throughout the day to take advantage of the patient's physiologic blinking, the treatment strips 10, 12 may also be used while the patient is resting or sleeping or while the patient simply maintains their eyes closed.

Figure 3A:
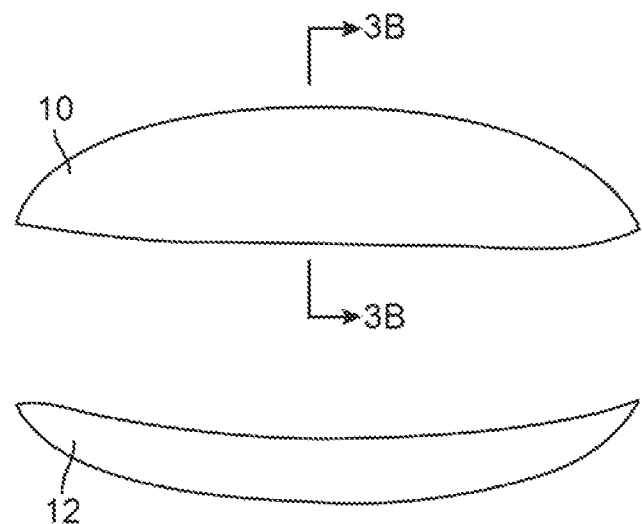
FIG. 3A shows an example of a contoured treatment strips.
Figure 3B:
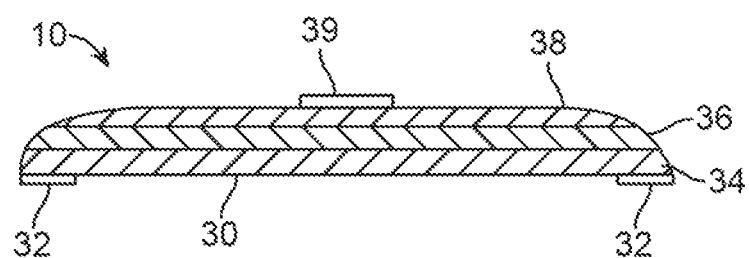
FIG. 3B shows an example of a cross-sectional side view of a treatment strip.

The treatment strips 10, 12 are desirably flexible enough to accommodate movement of the upper eyelid UL and/or lower eyelid LL which may move as much as about 15 mm or more. Thus, the treatment strips 10, 12 may be fabricated from various materials. FIGS. 3A and 3B show front and cross-sectional side views, respectively, in one example of a treatment strip configured to have an adhesive 32 positioned about a periphery of the strip to leave a contact region 30 for direct placement against the skin surface. The contact region 30 may further include a moisturizing layer to interface between the strip and skin to facilitate heat transfer from the strip as well as to provide moisturizing therapy to the skin. Alternatively, the treatment strips may be used with any number of moisturizing agents which may be applied to the underlying skin by the patient P or by a practitioner separately from the treatment strips. Moreover, the contact region 30 may be formed to have a surface which is smooth, porous, irregular, corrugated, etc. to facilitate contact and transfer of the heat from the treatment strip to the skin surface. Alternatively, the entire contact region 30, including its periphery, may be adhesive to maintain good contact. It may be hinged or curved to allow flexing or accordion-like dynamic movement for comfort and better, physiologically-sound ergonomics. In use, the strip may be applied under tension, as shown by the tensioned strip 10' in FIG. 3D, to further reduce any impairment to blinking and once adhered to the skin the strip may be released to allow for its flexion, as shown by the released strip 10" also in FIG. 3D, to facilitate blinking by the patient P.

In this variation, the treatment strip 10 may be configured to have a contact layer 34 (e.g., fabricated from conductive materials such as metals, alloys, porous ceramics, engineering ceramics, woods, polymers, composites, foams, polymer foams, elastomers, etc.) which may protect the skin from burns or any other adverse effects. A second heating layer 36 may be positioned above the contact layer 34 (or directly in contact against the skin) for generating the heat energy and an insulative layer 38 may be positioned atop the heating layer 36 for focusing, directing, or reflecting the heat towards the underlying skin surface as well as to protect the patient from contact with the heating layer 36 from other parts of the body. The insulative layer 38 may accordingly be fabricated from a variety of insulative materials, e.g., foams, foam tapes, gauze, silicone, microporous polyethylene films, metals, alloys, reflective materials, mirrors, etc. Moreover, the thickness of the treatment strip 10 may vary, e.g., anywhere from about 1/64" to 1/8" or more, depending upon the heating layer 36 mechanism as well as the desired thermal profile and targeted transmission temperature. Additionally and/or alternatively, the insulative layer 38 may be comprised of a thermochromic material which may change its color when a targeted temperature has been reached by the treatment strip 10 to indicate to the patient that the targeted temperature has been achieved or when the therapy has been completed.

The heating layer 36 may be configured to generate its heat energy, e.g., up to a temperature range of about 20° to 55° C. (or more) or between 40° to 50° C., through any number various mechanisms such as mechanical, electrical, or chemical mechanisms. In one variation, the heating layer 36 may comprise an air-activated warmer that can increase to an elevated treatment temperature for a period of time lasting, e.g., from 5 minutes up to 24 hours or even longer. An example can include air activated layer incorporating, e.g., iron. Other examples may incorporate a heating layer 36 containing, e.g., cellulose, iron powder, water, activated carbon (to speed up reaction), vermiculite (water reservoir), and salt (catalyst), saw dust, sodium chloride and water, etc. to generate heat from an exothermic oxidation of iron when exposed to air. Other variations may comprise a heating layer 36 which incorporates light-based activation (visible or UV-light powered) or use of a supersaturated solution (crystallization-type) to initiate and/or maintain an exothermic reaction.

Figure 3C:
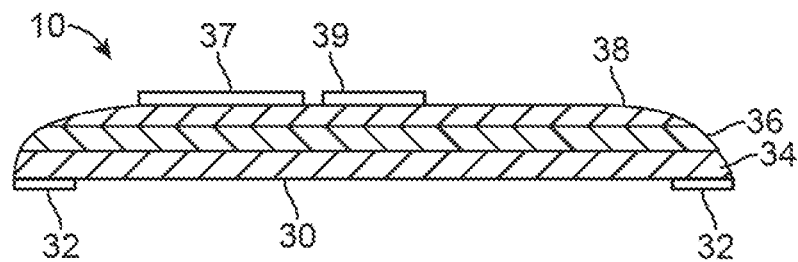
FIG. 3C shows another variation of a treatment strip which may optionally incorporate a controller.
Figure 3D:
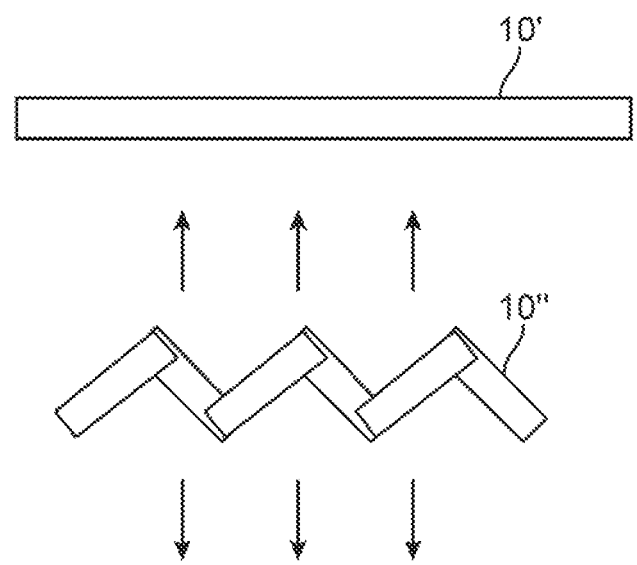
FIG. 3D shows yet another variation where a treatment strip may be formed into a zig-zag or curved configuration to facilitate the blinking by the patient.

Optionally, aside from use of a thermochromic material to determine when the treatment strip has reached a particular temperature, a separate temperature sensor 39 (e.g., thermocouples or thermistor devices) may be incorporated onto the treatment strip 10, as shown in FIG. 3B, attached either to the top of the strip or to the bottom of the strip. The treatment strip 10 may also incorporate an optional controller and/or display 37 having a processor which may be programmable and which may incorporate a separate on/off feature, as shown in FIG. 3C. The temperature sensor 39 may be in communication with the controller 37 which may be programmed to regulate the temperature of the heating layer 36 and/or a length of time for a particular treatment. The controller 37 may accordingly be programmable by a physician or caregiver or directly by the patient. Alternatively, the controller 37 may be configured to be inaccessible by the patient but may merely provide temperature and/or time indications for display to the patient. In the event that the controller 37 is programmable, the controller 37 may be programmed, e.g., to set a length of a heating period, set treatment times, set predetermined temperature ranges, control a heating temperature profile (such as gradually increasing the heating temperature or decreasing temperature over a predetermined period of time), etc.

In another variation, the heating layer 36 may generate heat through exothermic crystallization of supersaturated solutions (typically sodium acetate) which are usually reusable. The treatment strips may be recharged by heating them, e.g., by boiling, and allowing them to cool. Heating of these treatment strips may triggered by snapping a small metal device buried in the treatment strips which generates nucleation centers that initiate crystallization. Heat is required to dissolve the salt in its own water of crystallization and it is this heat that is released when crystallization is initiated.

In yet another variation, the heating layer 36 may comprise a battery operated warmer which utilizes electrically resistive heating elements that are used to convert electrical energy in the battery to thermal energy. The power supply may be internal or external to the treatment strips and the treatment strips may charged, e.g., by direct electrical contact, induction, etc.

Other mechanisms which may be incorporated into the heating layer 36 may comprise chemically actuated reactions such those used by sodium acetate heating pads. For instance, a single-use chemical reaction utilizing the catalyzed rusting of iron or dissolving calcium chloride may be use where the reagents are maintained in separate compartments within the treatment strips. When the patient squeezes the treatment strips, the compartments may break and the reagents mixed to produce heat. Examples may include use of a supersaturated solution of sodium acetate ($NaCH_3COO$) in water where crystallization may be triggered by flexing a small flat disc of notched ferrous metal embedded in the liquid which act as nucleation sites for the crystallization of the sodium acetate into the hydrated salt (sodium acetate trihydrate). Because the liquid is supersaturated, this makes the solution crystallize suddenly which releases the energy of the crystal lattice.

Yet another example of use in the heating layer 36 may include the use of a hot gel containing a supersaturated solution of a salt. Heat may be generated when the crystallization of the given salt occurs exothermically. Such heating layer 36 may be reused by forcing the salt back into solution within the heating layer 36.

Yet other examples for incorporation into the heating layer 36 may also include the use of high specific heat capacity materials which may be heated, e.g., by placement in a microwave prior to use, and then allowed to release the heat over a specified period of time.

Although the application of heat energy from the treatment strips is described, other variations may alternatively include the application of using the treatment strips for cooling of the underlying skin. Rather than using the heating layer 36 in an exothermic reaction, the layer may be configured to utilize an endothermic reaction instead to provide for cooling of the skin at temperatures ranging, e.g., from about 0° C. to 37° C. or more particularly from about 25° C. to 35° C. One example may include having the layer 36 to incorporate water and ammonium nitrate or ammonium chloride. Mixture of the water and the ammonium may reduce the temperature of layer 36. Another variation may include the use of cooling gel made by adding hydroxyethyl cellulose or vinyl-coated silica gel which may be cooled or frozen prior to use. Alternatively, cooling may be achieved by application of a cooling element such as a Peltier junction. Cooling, rather than heating, may be applied for conditions such as reducing inflammation, alleviating allergies or tired eyes, etc. particularly as the patient rests or sleeps. One example includes treatment for allergic conjunctivitis where application of the cooling treatment may provide relief from any burning or itching sensations by serving as a vasoconstrictor to limit blood flow, reduce blood vessel leakage and permeability thereby reducing acute swelling and inflammation. Yet another example includes reducing inflammation and fibrosis of a conjunctival bleb resulting from a trabeculectomy or mitigating inflammation generally following any ophthalmic surgical procedure.

Given the multitude of various mechanisms for incorporating a heating layer 36, the treatment strips may be configured to be single-use disposable strips, multiple-use disposable, re-usable strips, selectively actuatable, etc.

Aside from the application of heat energy from the treatment strips, the strips may also include a layer for the diffusion or release of one or more pharmaceutical, biological, or chemical agents either alone or in combination with the heat treatment. For instance, the pharmaceutical, biological, or chemical agents may be incorporated into the either the contact layer 34, insulative layer 38, or in a separate layer entirely, for transdermal delivery to the meibomian glands or to the areas surrounding the meibomian glands for additional and/or alternative treatments. For instance, examples of some of the various pharmacological agents which may be incorporated into the treatment strips (for use with or without the heat treatment) may include, but are not limited to, anti-inflammatory compounds, antibiotics, topical tetracycline, oral tetracycline, topical corticosteroids, oral corticosteroids, topical androgens, metronidazole, steroid antagonists, topical androgen analogues, TGF-β, omega 3 or omega 6 compounds, vasoconstrictors such as naphazoline, oxymetazoline, phenylephrine, and tetrahydrozoline, enzymes that promote lipid production, agents that stimulate production of enzymes that promote lipid production, agents that act as a secretagogue to enhance meibomian gland secretion, agents that replace or promote production of any tear component, cholinergic, muscarinic, or nicotinic agonists may be used, cosmeceuticals such as retinol or hyaluronic acid (HA) for wrinkled, puffy, or sagging skin in the cosmetics space, retinoic acid for acne, or agents that degrade or break down lipids like lipases, etc.

Other agents may include, e.g., alpha-melanocyte-stimulating hormone or adrenocorticotropic hormone or androgens like testosterone to increase tear production, agents which stimulate the underlying muscles like the orbicularis oculi or muscle of Riolan to stimulate blinking, increase frequency of blinking, or maintain longer closure after a blink by inhibiting the levator palpebrae muscle to force a blink or eyelid closure or otherwise mechanically compress the meibomian glands or glands of Zeis or other goblet cells or accessory lacrimal glands.

Additionally and/or alternatively, other agents for incorporation into the treatment strips may further include, e.g., neurotransmitters, noxious or irritating chemicals or vapors, hormones, oils, lipids, polar lipids, or fatty acids. Use of neurotransmitters may allow for stimulation to occur via second messenger pathways like activation of the Calcium/Protein Kinase C pathways, G-Protein activation, other calcium related pathways, calcium-calmodulin dependent protein kinases, the cyclic adenosine monophosphate dependent pathways, adenylyl cyclase pathways, inhibition of cAMP dependent phosphodiesterases.

In the event that the pharmacological or chemical agent is released during the heat treatment, the heat may help to improve penetration of any drugs into the underlying skin.

Yet another variation may incorporate a treatment strip which applies a heat rub that can be applied via the treatment strips onto the upper UL and/or lower eyelids LL for the treatment of the meibomian glands or which applies a compound which attracts light and heats up accordingly. Each of these variations may allow for the treatment strips 10, 12 to be applied and used while allowing for natural blinking to occur to facilitate the clearing of the ducts of melted oil blockages within the meibomian glands and to facilitate the spreading of the oil onto the tears.

Figure 4:
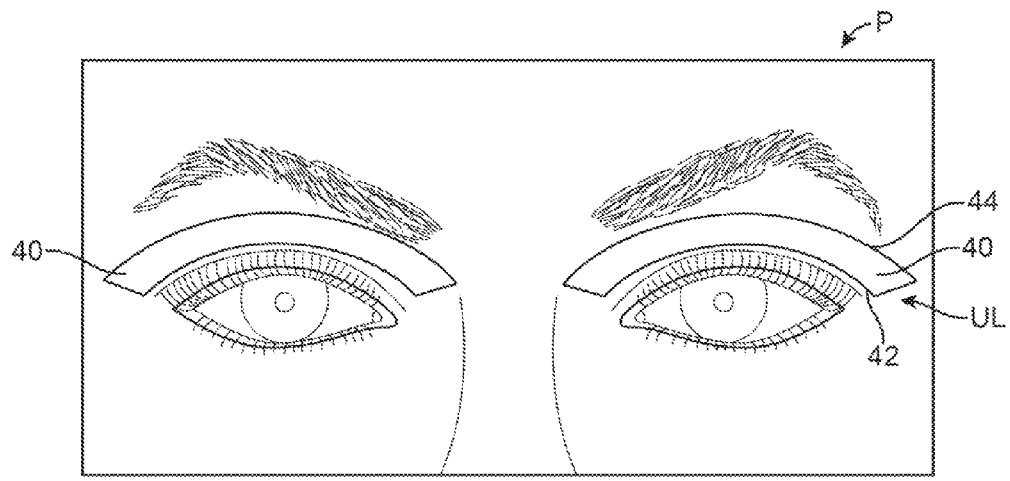
FIG. 4 shows a front view of another variation of the treatment strip which is relatively thin and positioned over the upper eyelids.

While the treatment strips may incorporate various layers into the strips to effect various different treatments, the strips may also be varied in size, shape, contour, etc. depending upon the desired treatment areas so long as the treatment strips are contoured or shaped to follow the location of at least one meibomian gland. An example of another configuration for the treatment strips is shown in the front view of FIG. 4, which illustrates a contoured thinned strip 40 sized and shaped for placement along the upper eyelid UL. This treatment strip may have a contoured lower edge 42 as well as a contoured upper edge 44 which follow the positioning of the underlying meibomian glands. Moreover, although the strips 40 are shown placed upon the upper eyelids UL of both eyes of the patient P, a single strip 40 may be used upon a single eyelid to selectively treat the particular meibomian glands in this and other examples shown herein. Additionally, one or both upper eyelids UL may be treated alone or in combination with one or both lower eyelids LL depending upon the desired treatment in this and other examples shown herein.

Figure 5:
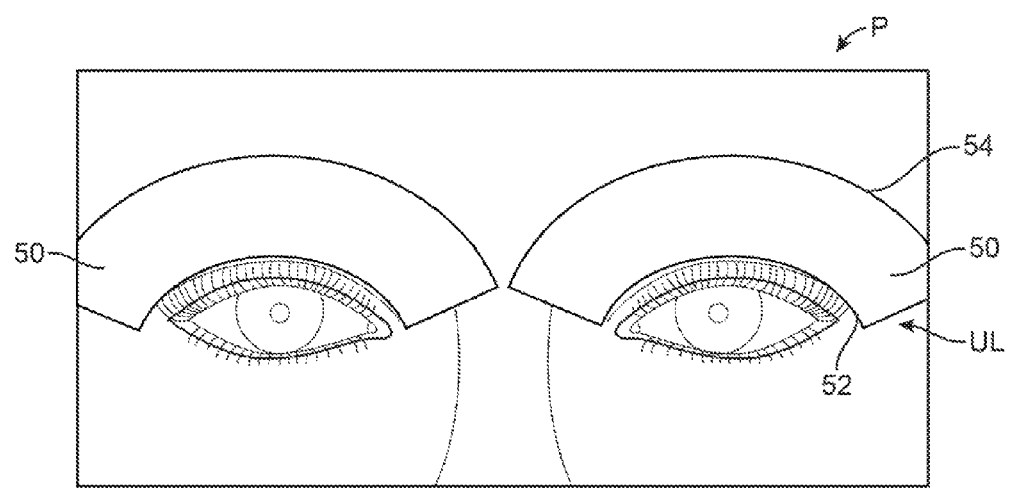
FIG. 5 shows a front view of another variation of the treatment strip which is relatively thick for treatment of the targeted meibomian glands as well as the surrounding tissue.

Another variation is shown in the front view of FIG. 5 which shows a contoured thickened strip 50 having a contoured lower edge 52 and contoured upper edge 54 for placement upon the meibomian glands as well as the surrounding tissue and glands. In yet other variations, rather than utilizing two separate treatment strips, a singular strip may also be used which extends over the bridge of the patient's nose. Additionally, the thickened strip 50 may cover the portions of skin farther proximally away from the eyelid margin to facilitate treatment. Because arterial blood supply to the eyelids proceed from proximal to distal of the eyelid margins, the treatment strip may heat (or cool) the blood supply as it continues to flow towards the eyelid margins. This early heating (or cooling) may provide a therapeutic effect for increased comfort to the patient, less impact on eyelid function (such as blinking), and increased safety of application and distance from the ocular surface as well as potentially increased efficacy allowing for more total heating or cooling therapy.

Figure 6:
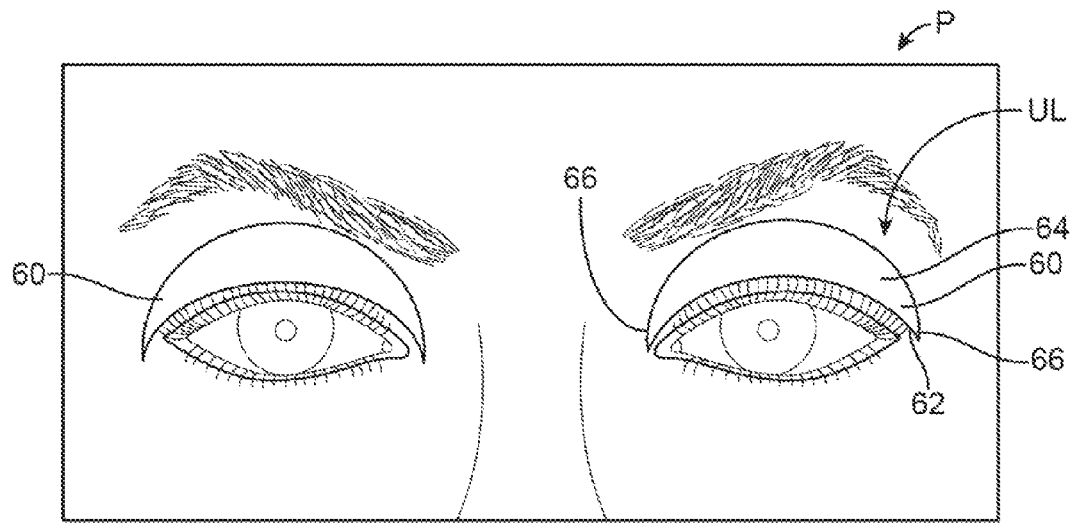
FIG. 6 shows a front view of another variation of the treatment strip which is contoured to more closely follow the meibomian glands in the upper eyelids.
Figure 7:
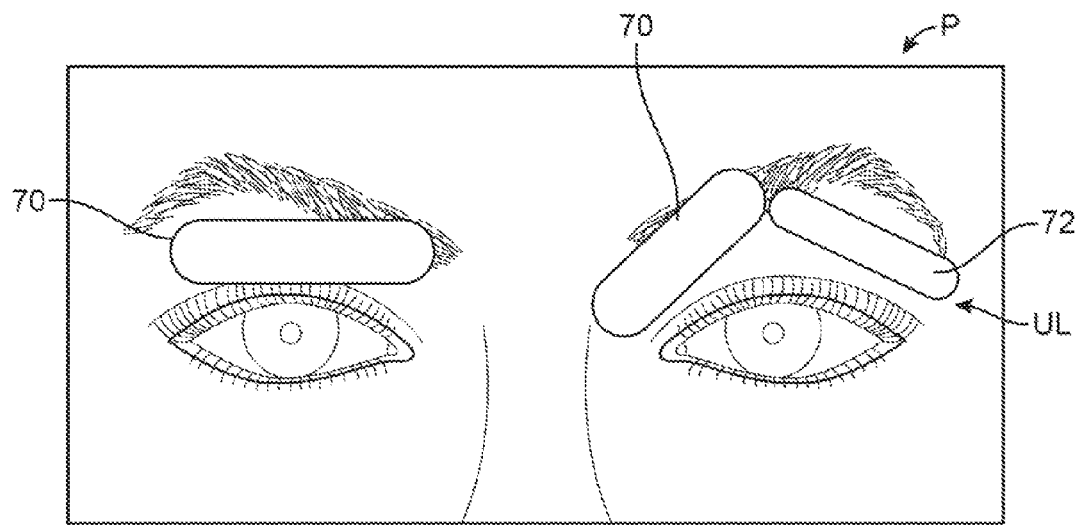
FIG. 7 shows a front view of another variation of the treatment strip which may be formed into shortened strips for selective placement along the eyelids.

FIG. 6 shows yet another variation having a contoured thinned strip 60 where the lower 62 edge and upper edge 64 converge to a tapered end 66 for placement upon the meibomian glands. FIG. 7 shows yet another variation where the treatment strips may comprise straightened strips 70 having a first width used in combination with a thinned straightened strip 72 as well. The straightened strips 70 may comprise straightened strips (having optionally rounded corners) which may be selectively placed over the meibomian glands. In this example, a single straightened strip 70 may be applied upon the upper eyelid UL of a single eye while the remaining eye may utilize a single straightened strip 70 applied along a first portion of the upper eyelid UL and a second straightened strip 72 having a relatively thinner width for placement upon a second portion of the upper eyelid UL. Each of the strips may be applied singularly or in various combinations depending upon the desired treatment areas and are shown in this variation as an exemplary combination.

Figure 8:
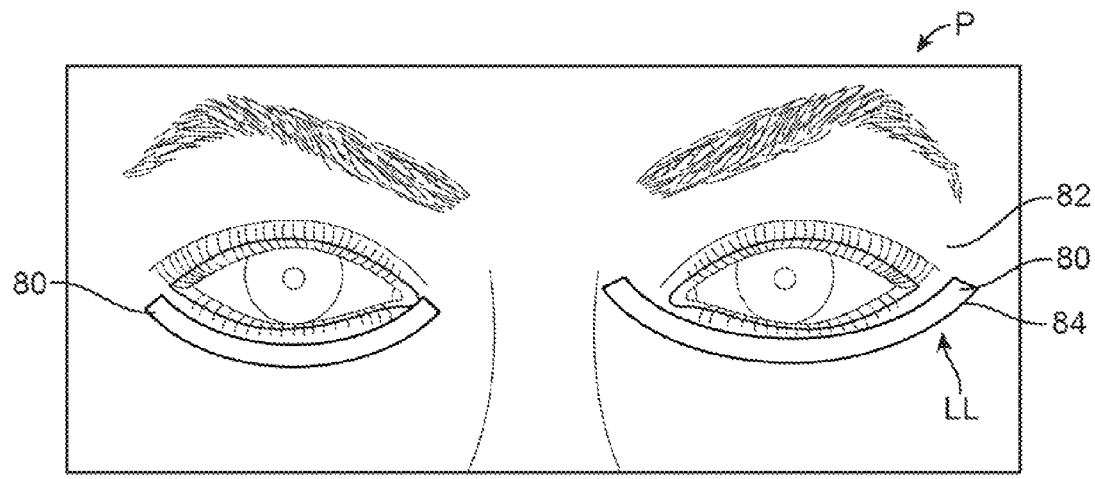
FIG. 8 shows a front view of another variation of the treatment strip which is relatively thin and contoured for placement along the lower eyelids.

In the variation of FIG. 8, an example of contoured thinned strip 80 is shown applied along the lower eyelid LL. As illustrated, the contoured upper edge 82 and contoured lower edge 84 may be contoured to follow over the underlying meibomian glands. As described above, the treatment strips may be applied singularly over one or both eyes or they may be applied in combination with treatment strips applied over one or both eyes of the upper eyelids. Moreover, any of the treatment strips shown herein may be used in any number of combinations with one another.

Figure 9:
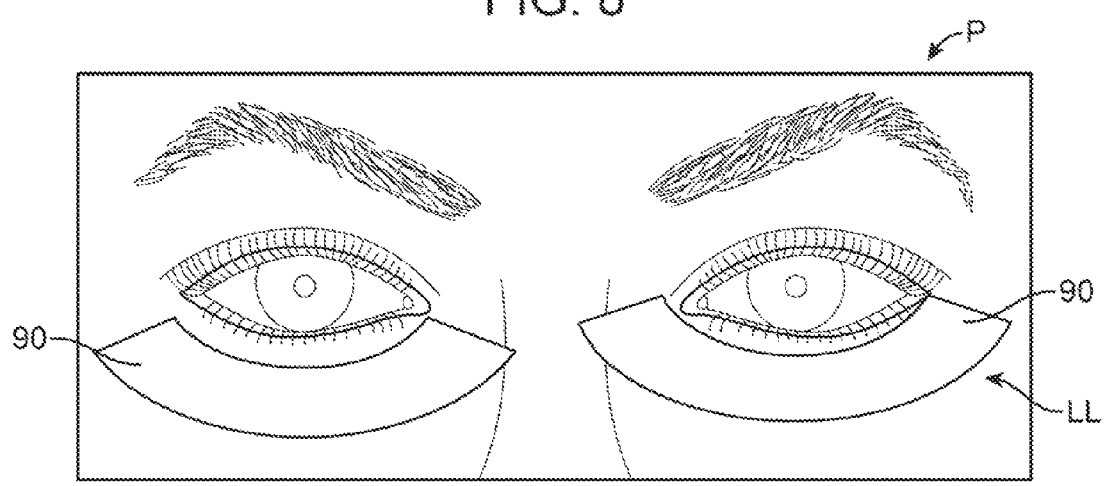
FIG. 9 shows a front view of another variation of the treatment strip which is relatively thicker and also contoured for placement along the lower eyelids.
Figure 10:
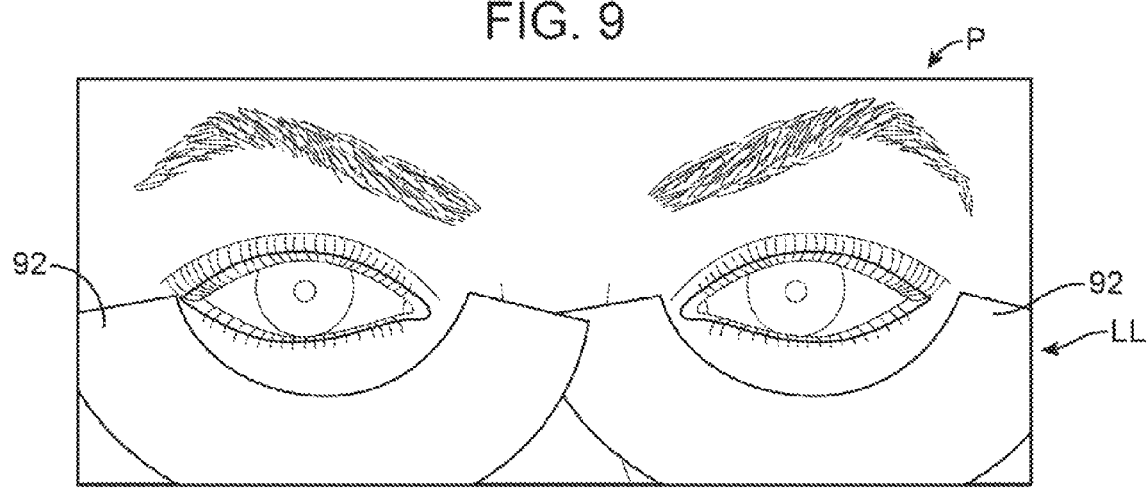
FIG. 10 shows a front view of another variation of the treatment strip which is relatively thick for placement along the lower eyelids.

FIG. 9 shows another variation where the contoured thickened strip 90 may be applied over the lower eyelids LL and may further have a width which is relatively wider than those treatment strips shown above in FIG. 8. Similarly, FIG. 10 shows yet another variation where the contoured thickened strip 92 may have a width which is relatively wider still for treating not only the underlying meibomian glands but also any glands and tissue surrounding the peri-orbital region. As described above for the variation of FIG. 5, the widened treatment strip may heat (or cool) the blood supply as it continues to flow towards the eyelid margins. The early heating (or cooling) may provide a therapeutic effect for increased comfort to the patient, less impact on eyelid function (such as blinking), and increased safety of application and distance from the ocular surface.

Figure 11:
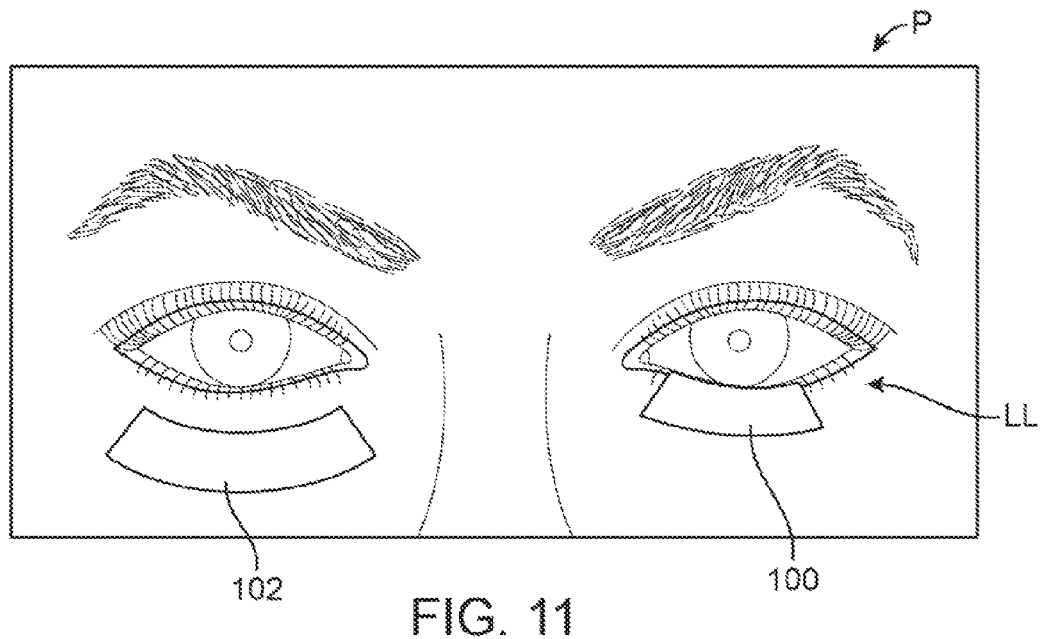
FIG. 11 shows a front view of another variation of the treatment strip which is contoured for the lower eyelids and which may be shortened into various lengths.
Figure 12:
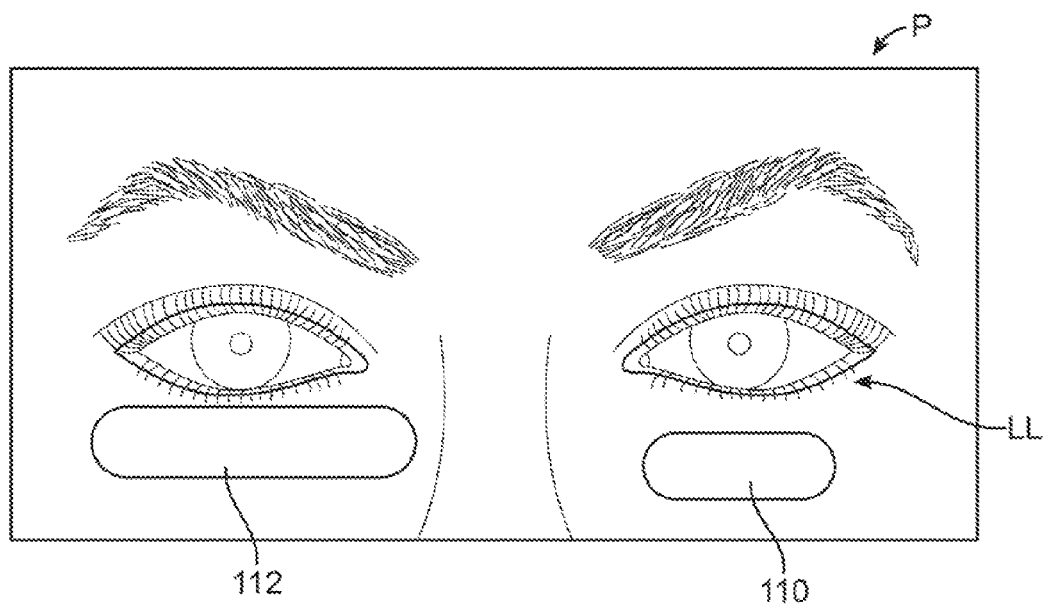
FIG. 12 shows a front view of another variation of the treatment strip which is relatively straightened and selectively shortened.

Aside from variations in width of the treatment strips, any of the treatment strips may be varied in length as well to selectively target portions of the meibomian glands or particularly selected meibomian glands. For example, FIG. 11 shows one variation where the shortened contoured strip 100 having a first shortened length may be applied upon the lower eyelid LL (and/or upon the upper eyelid UL). A second contoured strip 102 having a second length which is longer than the shortened contoured strip 100 may also be seen for comparison. FIG. 12 similarly shows a shortened and straightened strip 110 applied upon the lower eyelid LL and a second straightened strip 112 having a relatively longer length applied upon the second lower eyelid LL. The straightened strips 110, 112 may incorporate rounded ends and may be varied in length depending upon the desired treatment area. They could also be rounded or circular to cover one or more styes.

Figure 13:
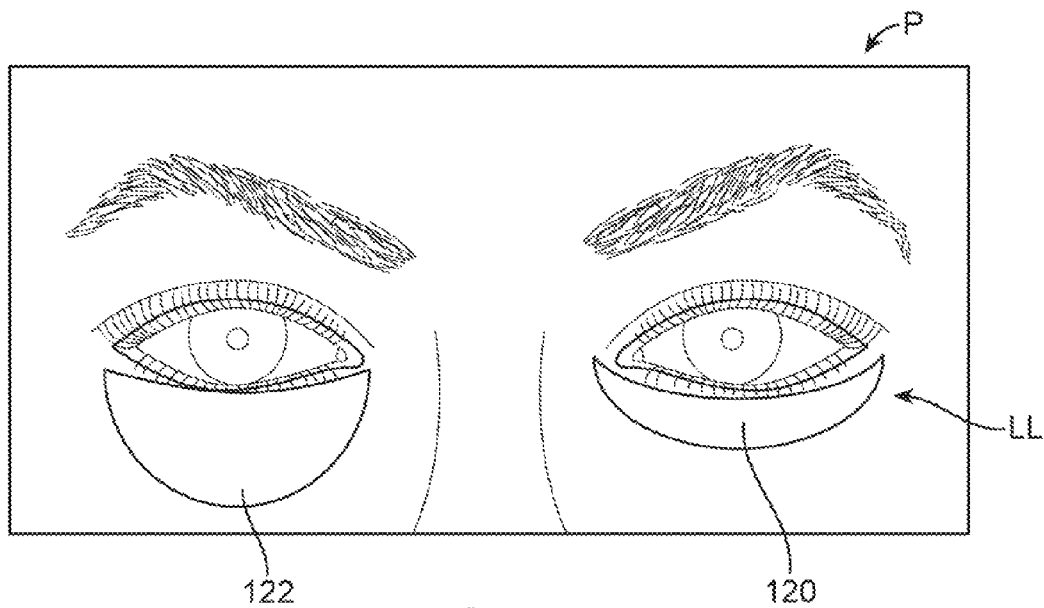
FIG. 13 shows a front view of another variation of the treatment strip which is contoured and further illustrates how differently sized strips may be used in combination with one another.

FIG. 13 shows yet another variation where the contoured strips 120 may be configured to have tapered ends for overlying the meibomian glands. In comparison, thickened contoured strip 122 is also illustrated having tapered ends yet is relatively wider to alter the treatment area.

Figure 14:
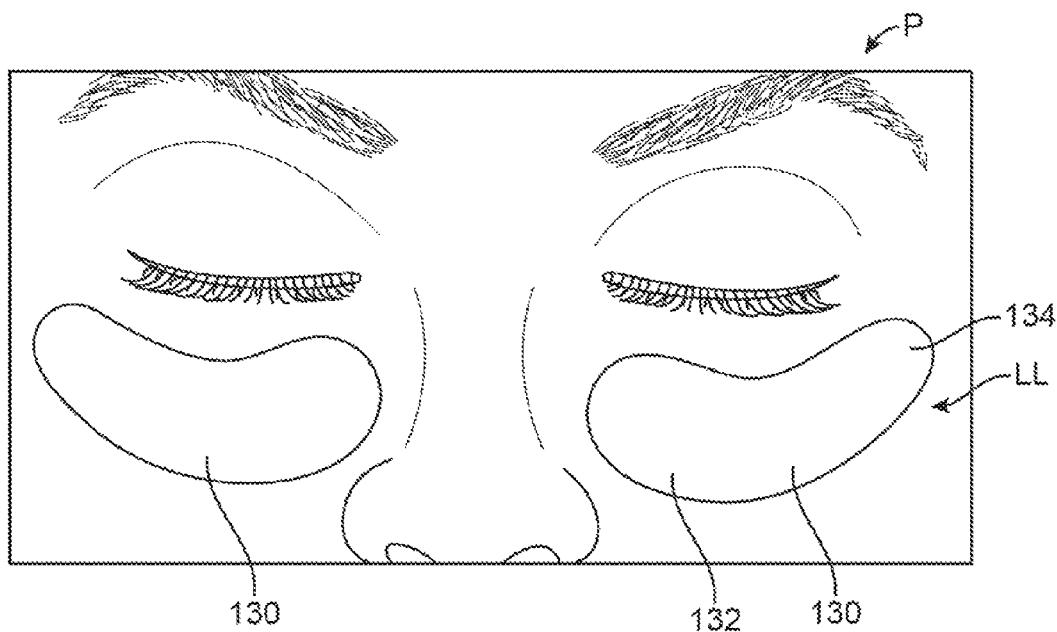
FIG. 14 shows a front view of another variation of the treatment strip which is sized to follow not only the meibomian glands along the lower eyelid but also the surrounding tissue regions.
Figure 15:
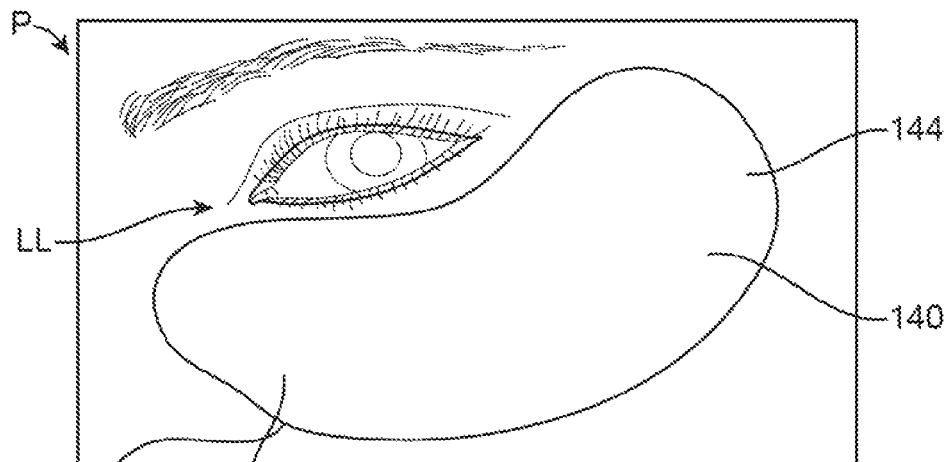
FIG. 15 shows a front view of another variation of the treatment strip which is contoured to follow the meibomian glands along the lower eyelid along with the surrounding tissue regions.
Figure 16:
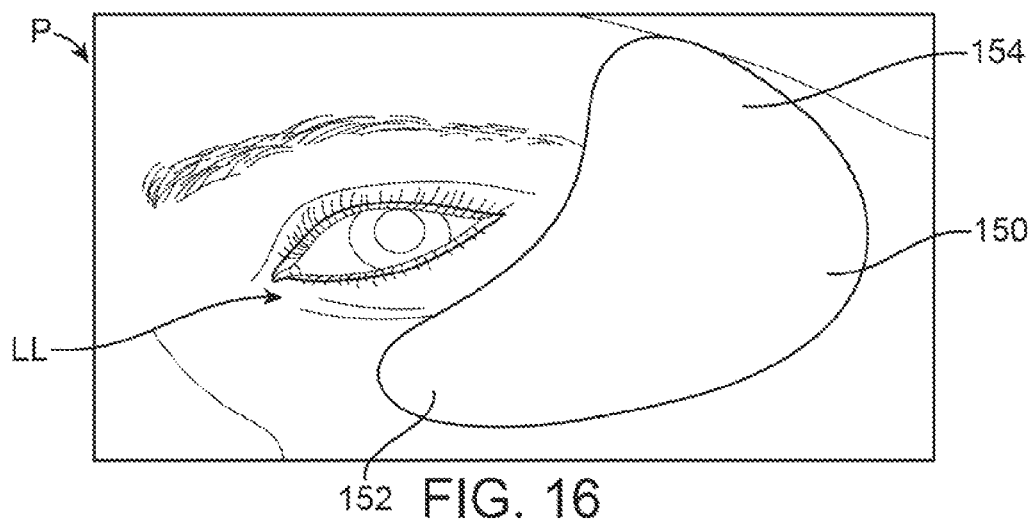
FIG. 16 shows a front view of yet another variation where the strip is contoured to follow at least a portion of the meibomian glands but also to cover selected regions of the surrounding tissue.

FIG. 14 shows another variation where the contoured strip 130 may have a first portion 132 which is relatively wider than a second portion 134 for placement over the meibomian glands of the lower eyelid LL. Each of the first 132 and second portions 134 may be varied in width again depending upon the desired treatment areas. Another example is shown in FIG. 15 which shows a contoured strip 140 having a first portion 142 and second portion 144 which are considerably wider for treating not only the meibomian glands along the lower eyelid LL but also the surrounding peri-orbital tissue regions such as the underlying maxillary sinus. FIG. 16 shows yet another example of a contoured strip 150 having a first portion 152 and a second portion 154 which is wider than the first portion 152 and where the strip 150 is positioned to cover just a portion of the meibomian glands along the lower eyelid LL but also covers various other glands, such as the lacrimal glands, around the peri-orbital regions.

Figure 17:
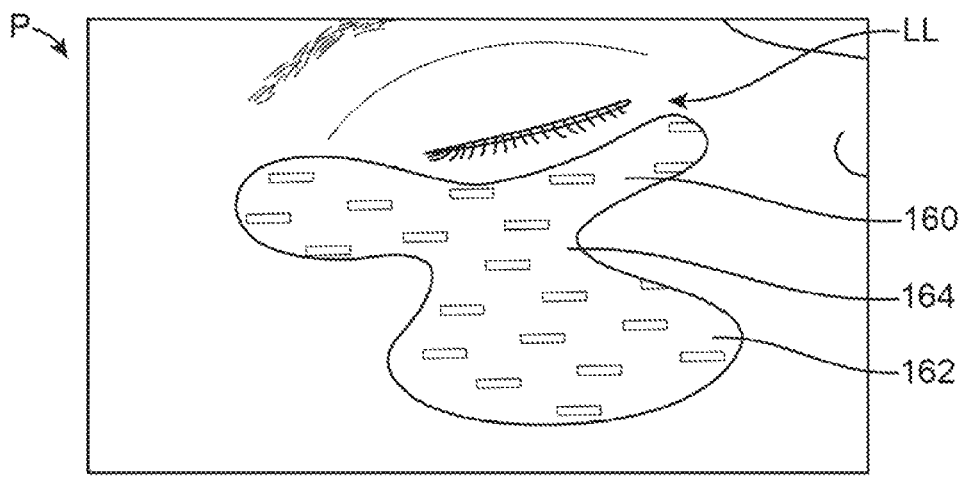
FIG. 17 shows a front view of yet another variation which is contoured to selectively treat particular regions of the underlying tissue.

FIG. 17 shows yet another variation of a treatment strip comprised of a contoured strip 160 having a secondary enlarged portion 162 attached via a connecting strip 164. While the contoured strip 160 may treat the meibomian glands along the lower eyelid LL, the secondary enlarged portion 162 may treat region of the tissue along the cheeks of the patient.

Figure 18:
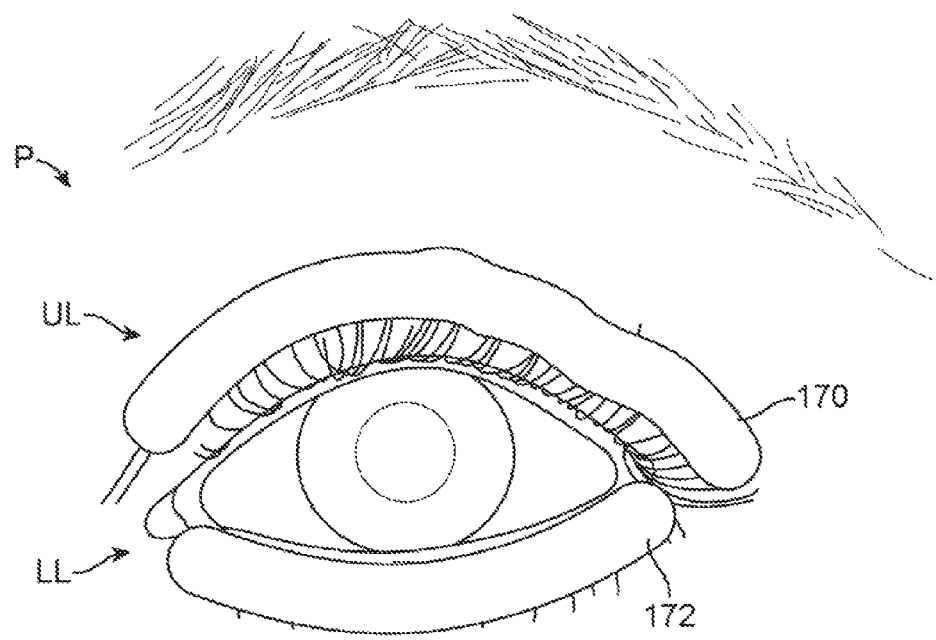
FIG. 18 shows a front view of yet another variation where the contoured treatment strips may be used in combination for treating both upper and lower eyelids.
Figure 19:
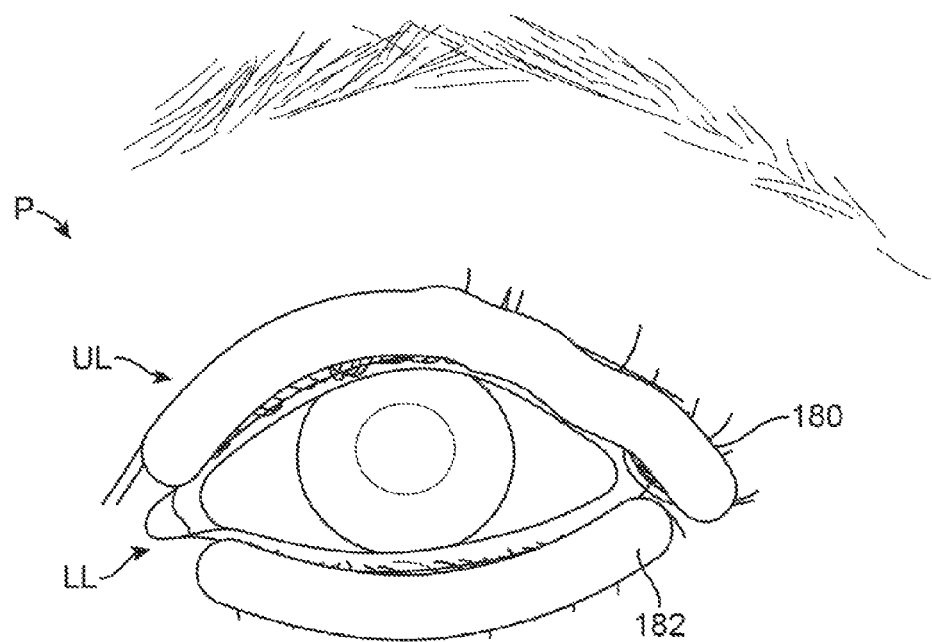
FIG. 19 shows a front view of yet another variation where the treatment strips may be altered in color to more closely match the underlying skin tone.

In yet another variation, FIG. 18 shows an example where both an upper contoured strip 170 and a lower contoured strip 172 may be applied, respectively, along the upper eyelid UL and lower eyelid LL. As discussed previously, the contoured strips 170, 172 are shaped and applied to follow the underlying meibomian glands while enabling the patient P to blink normally. FIG. 19 shows a similarly applied upper contoured strip 180 and lower contoured strip 182 where the strips may be varied in color to more closely match a skin tone or shade of the patient P. Because the treatment strips may be used throughout the day for any given period of time, the strips 180, 182 may be made in various colors or tones to either more closely match the skin tone or shade of the patient P.

Figure 20:
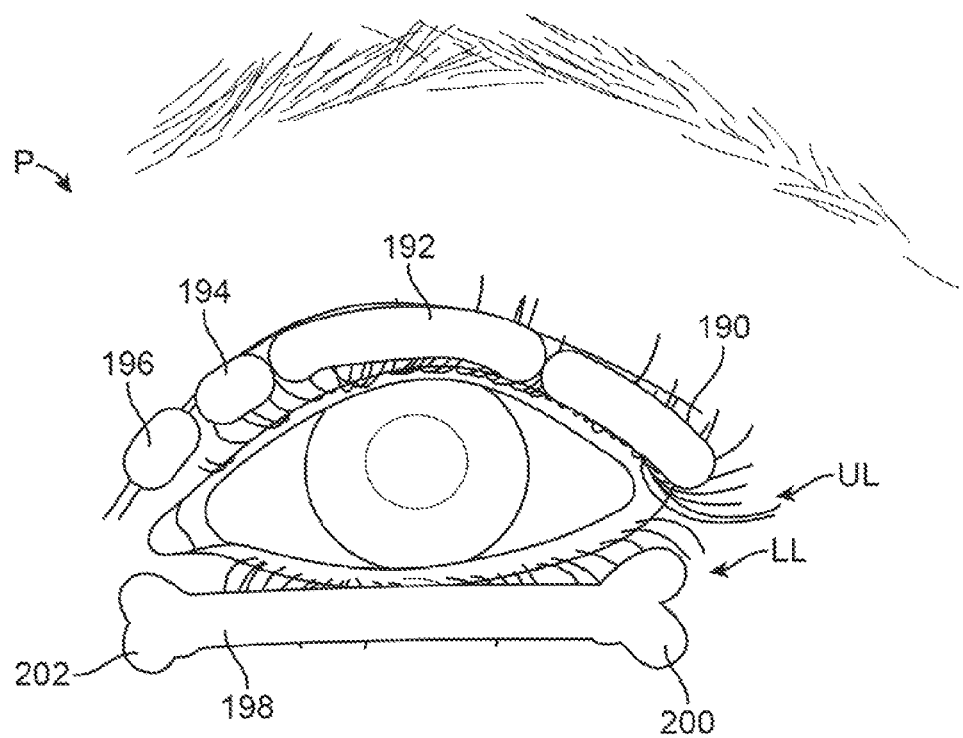
FIG. 20 shows a front view of yet another variation where the treatment strips may be sized to treat specified meibomian glands.
Figure 21:
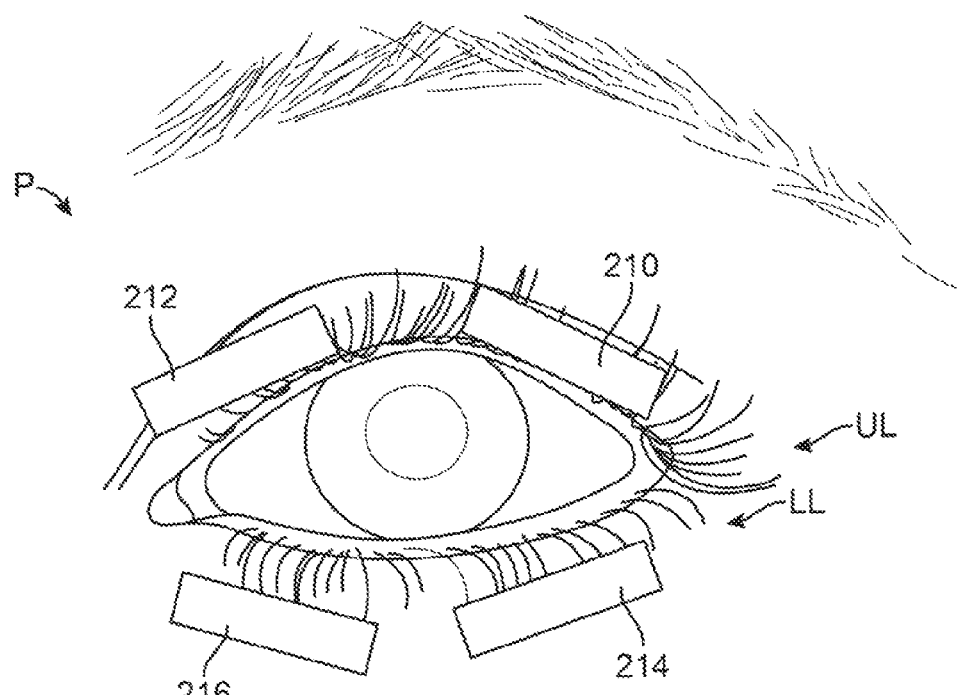
FIG. 21 shows a front view of yet another variation where the strips may be varied in size to selectively treat particular meibomian glands.

In yet another variation, FIG. 20 shows another example where the treatment strips may be varied in length to treat specific regions along the upper UL or lower eyelids LL. In this example, a first upper strip 190 having a first length may be applied adjacent to a second upper strip 192 having a second longer length. Optionally, a third upper strip 194 and/or fourth upper strip 196 having lengths which are relatively shorter may also be applied as well over selected meibomian glands. A lower strip 198 having enlarged distal ends 200, 202 are also shown for placement along the lower eyelid LL. The distal ends 200 may be shaped to facilitate the placement and/or removal of the strip 198 from the skin (or for better adhesion). Yet another example is shown in FIG. 21 which illustrates several shortened treatment strips, e.g., first upper strip 210 and second upper strip 212, placed selectively along the upper eyelid UL along with, e.g., first lower strip 214 and second lower strip 216, placed selectively along the lower eyelid LL. Each of the strips may be varied in length as well as size depending upon the treatment area.

Figure 22:
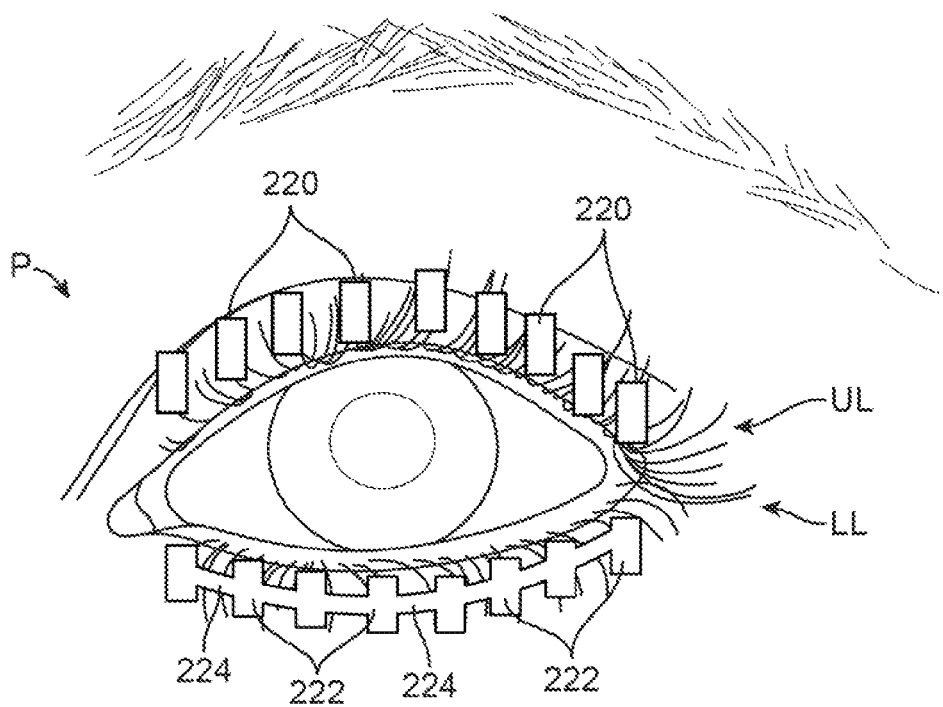
FIG. 22 shows a front view of yet another variation where the treatment strips may be sized to treat individual meibomian glands.
Figure 23:
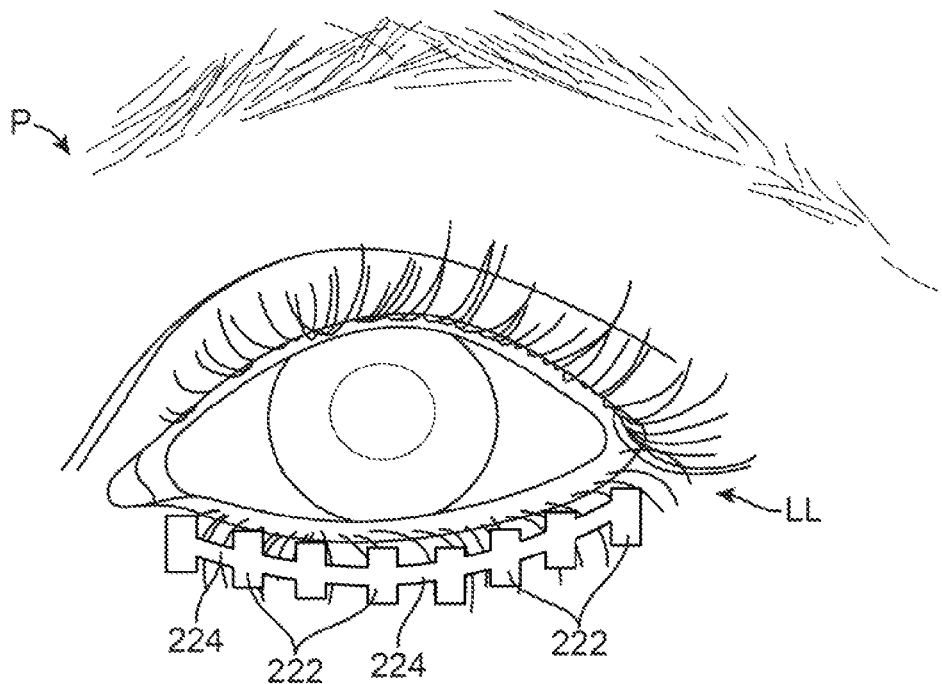
FIG. 23 shows a front view of yet another variation where the treatment strips may be sized for placement along the lower eyelids.

With the lengths of the treatment strips being variable, multiple strips may be applied adjacent to one another or to overlap horizontally and/or vertically along the eyelids. Moreover, one or more of the treatment strips may be made as a single unit or as a series of panels either horizontally or vertically oriented which may be optionally connected by a backing that is flexible. As shown in the variation of FIG. 22, each of the targeted strips 220 may have a length of, e.g., about 1 mm, to cover as few as a single meibomian gland. One or more of the targeted strips 220 may be applied along the upper eyelid UL and/or lower eyelid LL. Additionally, one or more of the targeted strips 222 may further comprise a connecting member 224 which functions as a backing to couple each of the individual targeted strips 222 to one another. The individual strips may be applied selectively at particularly problematic meibomian glands either along the upper eyelid UL and/or lower eyelid LL. For example, FIG. 23 illustrates the individual targeted strips 222 placed along just the lower eyelid LL.

While the treatment strips may be applied to one or more of the meibomian glands, variations of the strip may also be used to treat other glands such as the sebaceous glands, e.g., for acne treatment. Treatment strips used to treat acne may utilize different pharmacological treatments. Other glands in the underlying eyelids and conjunctiva CN for treatment may also include treatment of, e.g., the glands of Zeis GZ, goblet cells, accessory sebaceous glands, accessory goblet cells such as the Henle and Manz glands, accessory lacrimal glands of Wolfring GW or Krause GK, or either one or both lobes of the main lacrimal glands such as the palpebral portion or the orbital portion.

Moreover, the treatment strips may be used to potentially treat eye disorders beyond meibomian gland dysfunction including, e.g., blepharitis, sjogren's syndrome, dacryoadenitis, conjunctivitis, allergic conjunctivitis, keratoconjunctivitis sicca, keratitis, dacryocystitis, iritis, keratitis, retinitis, sclerokeratitis, uveitis, contact lens related eye problems, post blepharoplasty or eyelid or eye surgical procedures (e.g., cataract surgery, LASIK, PRK, etc.), absent or dysfunctional blinks disorders, conjunctivitis, blepharospasm, exposure keratopathy, lagophthalmos, lid myokymia, infections, styes, chalazion, hordeolum, glaucoma, blebs, trauma, etc.

Figure 24:
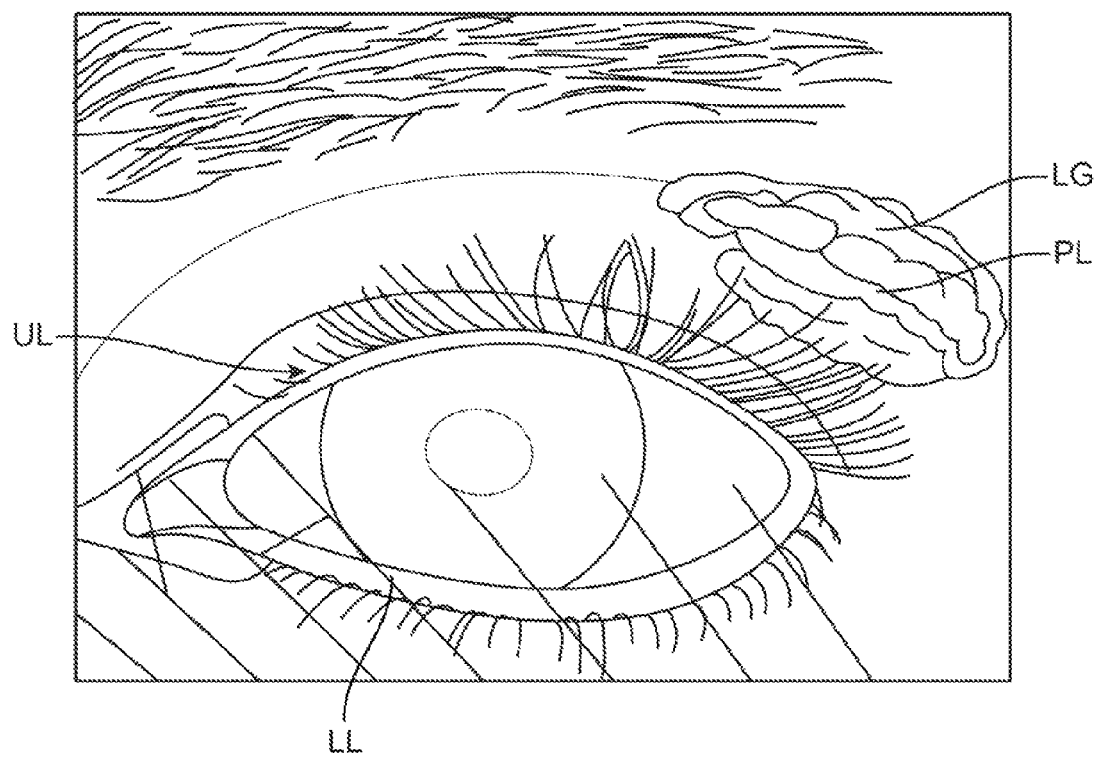
FIG. 24 shows a front view illustrating the relative positioning of the lacrimal glands.
Figure 25:
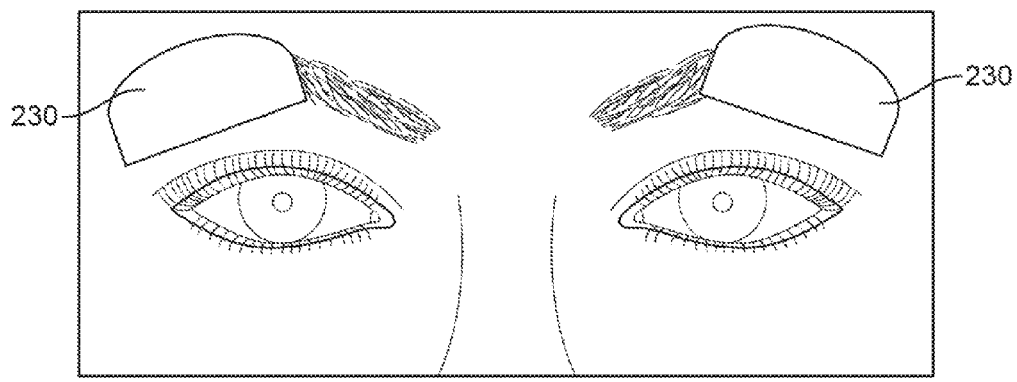
FIGS. 25 to 27 show variations of treatment strips which may be contoured and positioned for treating the underlying lacrimal glands.
Figure 26:
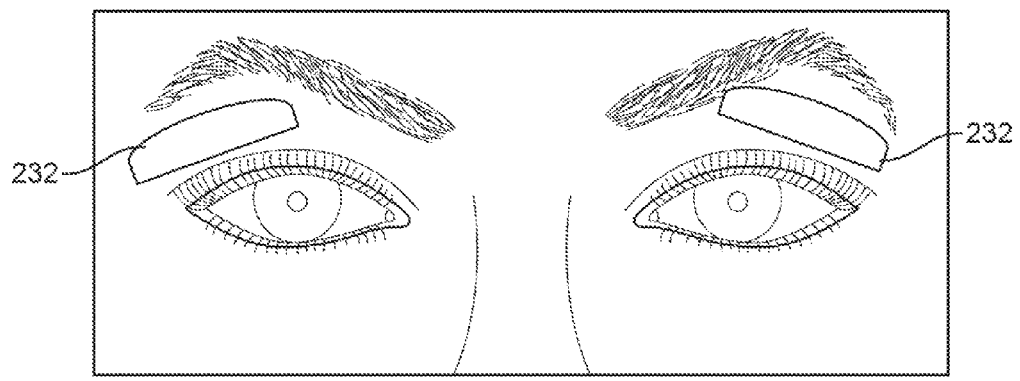
Figure 27:
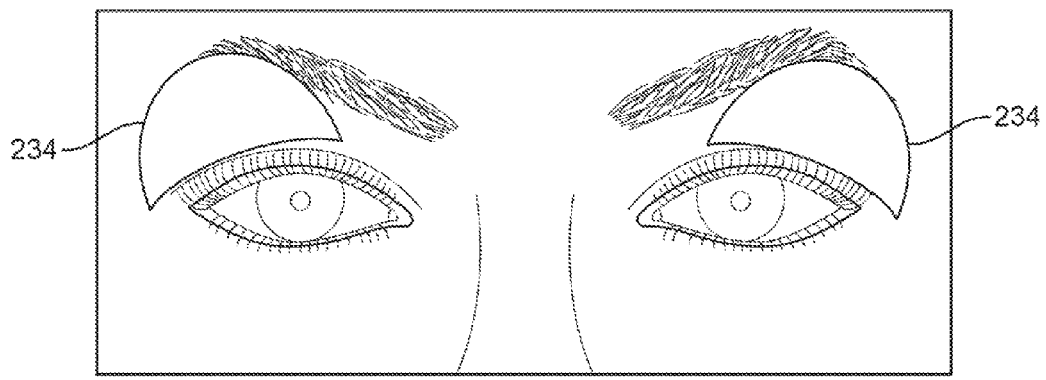

Yet another example, as mentioned above, may include use of the treatment strips for treating disorders of the lacrimal gland LG and/or palpebral lacrimal gland PL which are located above the eye as shown in FIG. 24. Variously sized treatment strips, such as lacrimal gland strips 230 shown in FIG. 25 which is sized to have a curved upper periphery, may be sized for placement directly over the skin surface above where the lacrimal glands LG are located. Other variations are shown in FIG. 26 which illustrates lacrimal gland strips 232 which are relatively thinner in width as well as in FIG. 27 which illustrates lacrimal gland strips 234 which have curved peripheries ending in tapered ends. The treatment strips may deliver heat, e.g., to stimulate the lacrimal gland LG, increase gland metabolism, activity, lacrimation, etc. Alternatively, the treatment strips may deliver cooling therapy to reduce inflammation which impairs gland function.

Figure 28:
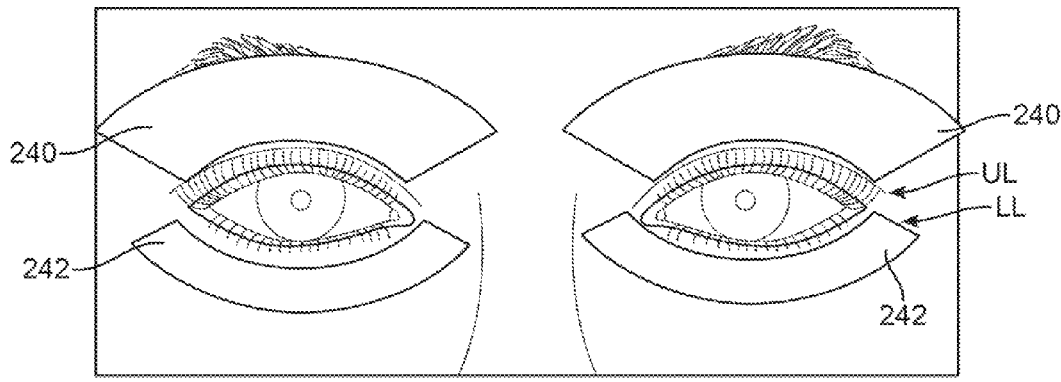
FIGS. 28 to 30 show variations of treatment strips which may be contoured and sized for treating the meibomian glands in combination with optionally treating the lacrimal glands as well.

The lacrimal glands LG and/or palpebral lacrimal gland PL may be treated alone or in combination with the treatment strips contoured for treatment of the meibomian glands. One variation is shown in FIG. 28 which illustrates contoured strips 240 which are enlarged in width to cover both the lacrimal glands LG as well as the meibomian glands along the upper eyelid UL. Contoured treatment strips 242 are also shown placed along the lower eyelids LL for treatment of the meibomian glands as well.

Figure 29:
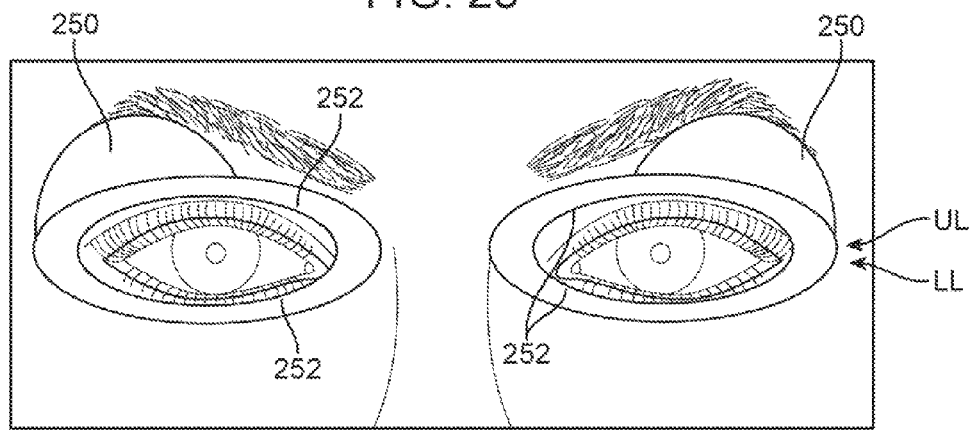
Figure 30:
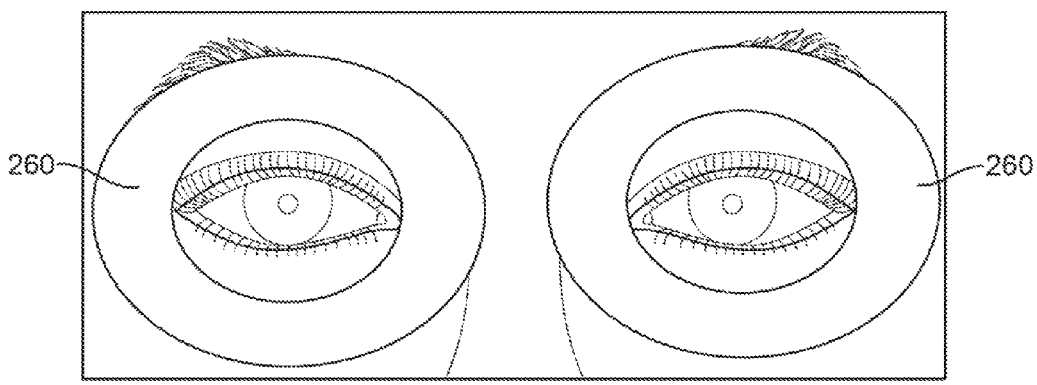

FIG. 29 shows another variation where lacrimal gland strips 250 may be placed over the lacrimal glands LG in combination with an integral combined contoured strip 252 which is sized to encircle the eyes entirely while following the location of the meibomian glands along both the upper eyelids UL and lower eyelids LL. This fully encircling design may also be held in place more tightly against the skin with a strap which may encircle the patient's head, if so desired. Another variation is shown in FIG. 30 which illustrates an integral combined contoured strip 260 which is also sized to encircle the eyes entirely and further having a width suitable for placement over the lacrimal glands LG.

Figure 31:
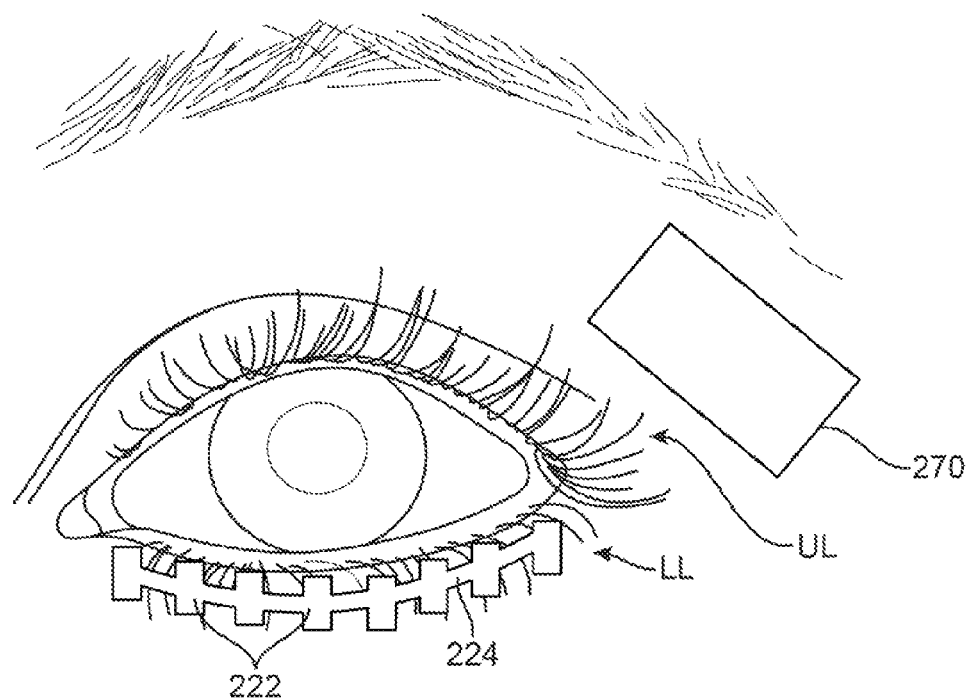
FIGS. 31 and 32 show variations on treatment strips which may be sized for selectively treating particular meibomian glands in combination with the lacrimal gland.
Figure 32:
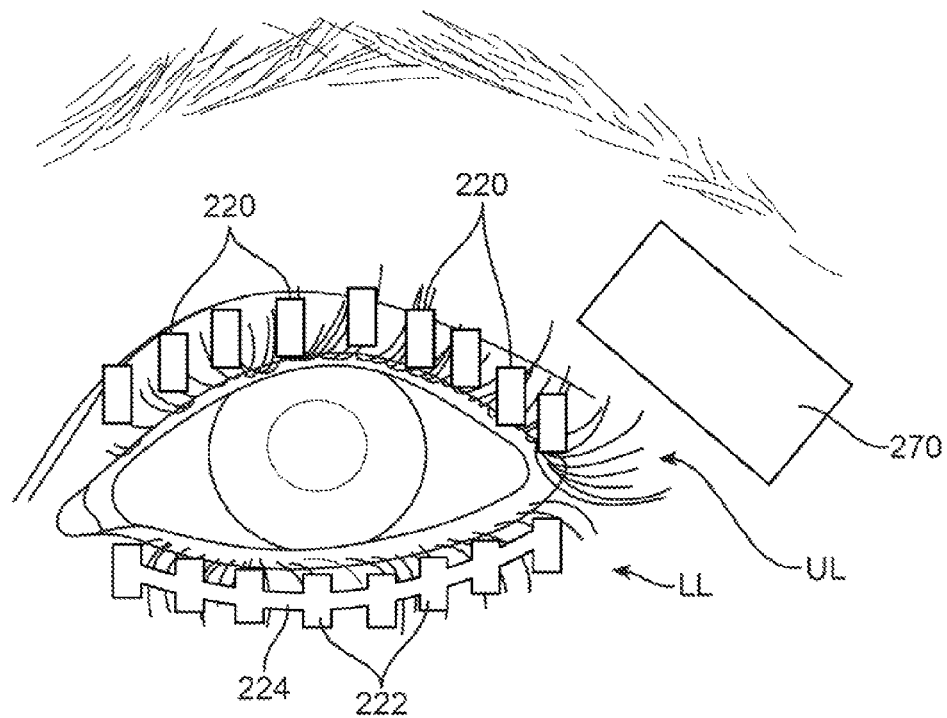

The lacrimal gland strip 270 may be used in combination with any of the treatment strips shown herein. Another example is illustrated in FIG. 31 which shows lacrimal gland strip 270 used in combination with the individual strips 222 while FIG. 32 shows yet another example where lacrimal gland strip 270 may be used in combination with not only the individual strips 222 but also the strips 220 located along respective lower eyelid LL and upper eyelid UL.

Figure 33:
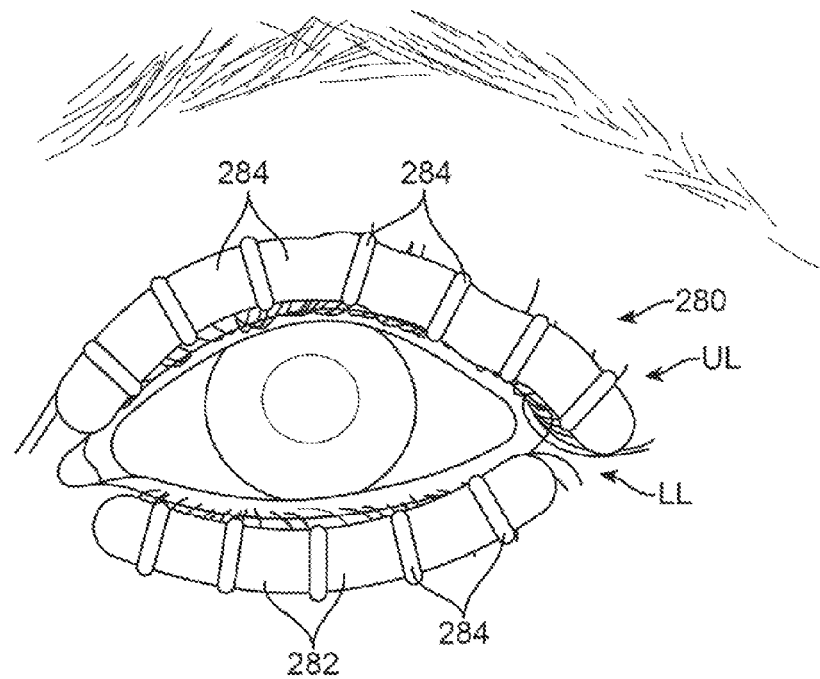
FIG. 33 shows another variation of a treatment strips which may have mechanically biasing features incorporated along the strips for applying a force to the underlying tissue and meibomian glands.

While the treatment strips may be applied over the meibomian glands to apply the heat energy, the treatment does not require the application of any external force applied by the strip or any other external device but may utilize the natural blinking of the patient to facilitate treatment, as described above. However, in additional variations, the treatment strips may be configured to apply both the heat treatment as well as an external force. Any number of mechanisms may be utilized to apply a pinching or biasing force to provide for compression of the underlying skin and of the meibomian glands during application of the heat therapy. One example is shown in the front view of FIG. 33 which illustrates a biased treatment strip 280 which may be comprised of a strip 282, as previously described, having one or more biasing mechanisms 284 positioned along the strip 282. The one or more biasing mechanisms 284 may be positioned along either the upper strip or lower strip or both, as shown.

Figure 34:
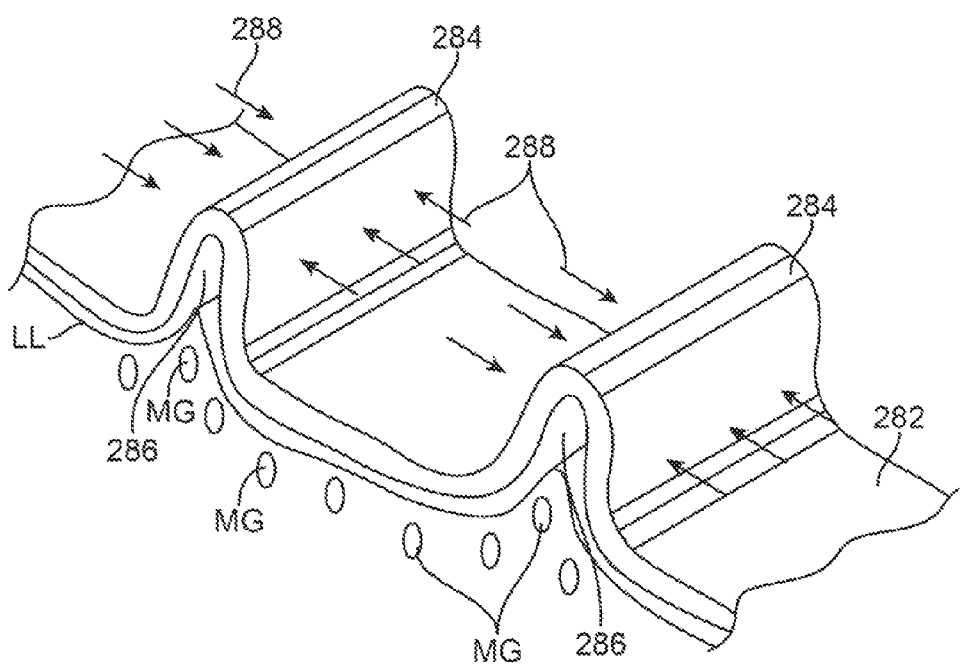
FIG. 34 shows a detail perspective view of the treatment strip of FIG. 33 illustrating an example of biasing mechanisms incorporated along the strips.

In this example, the biasing mechanism 284 may locally squeeze or compress the underlying skin to apply a pressure to the meibomian glands MG to facilitate the clearing of any obstructions, particularly if applied simultaneously with the heat treatment. An example of a biasing mechanism 284 is illustrated in the perspective view of FIG. 34 which shows how the biasing mechanism 284 may generally comprise portions of the strip 282 or separate members biased to form corresponding channels 286 which are configured to flex in an open or closed configuration. When the strip is initially placed upon the skin, the ends of the strip may be pulled to open the channels 286 which may then be placed upon the skin surface. As the strip and biasing mechanisms 284 relax, the underlying skin and meibomian glands MG may be compressed or pinched by the compression forces 288 induced into the biasing mechanism 284.

Figure 35:
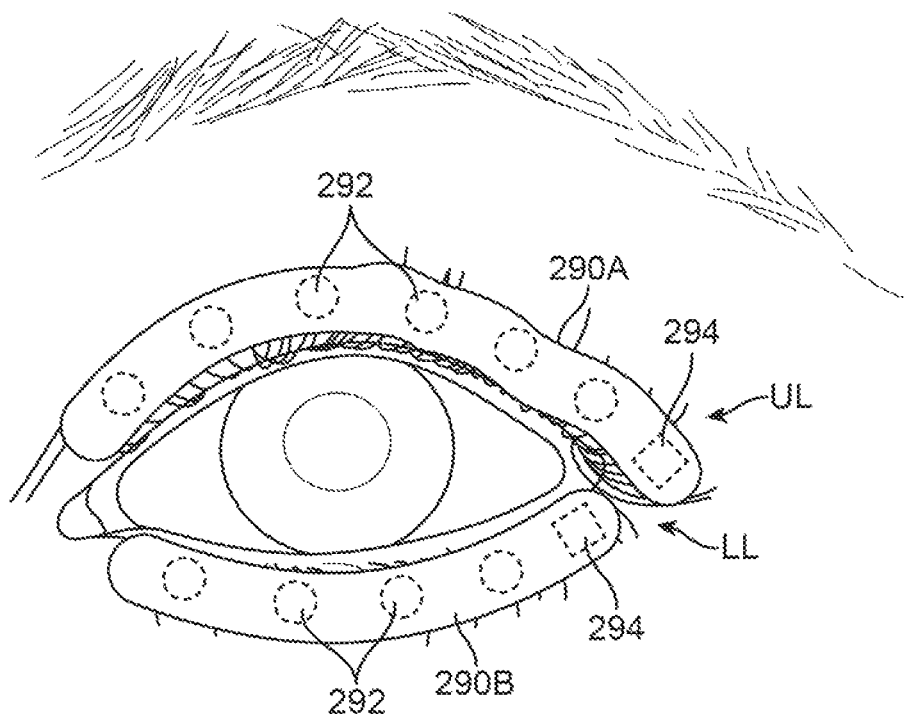
FIG. 35 shows another variation of treatment strips incorporating one or more transducers for imparting a vibrating force to the underlying tissue and meibomian glands.

Aside from a compression force, the strip may be formed with alternative components such as a mechanical component to impart vibrational energy to facilitate the expression of the meibomian glands and promote oil secretion. An example is illustrated in FIG. 35 which shows another variation of the contoured strip 290A, 290B having one or more vibrating elements 292 (e.g., piezoelectric transducers, electromagnetic actuators, eccentrically coupled rotating elements, etc.) incorporated along the strips 290A, 290B. The one or more vibrating elements 292 may be electrically coupled to a power supply and/or processor 294 also contained along the strips 290A, 290B. Moreover, the vibrational energy may be imparted separately from heat treatment or in combination with the heat therapy. The power supply may include a micro-battery which can be rechargeable to deliver microcurrents of energy.

Figure 36:
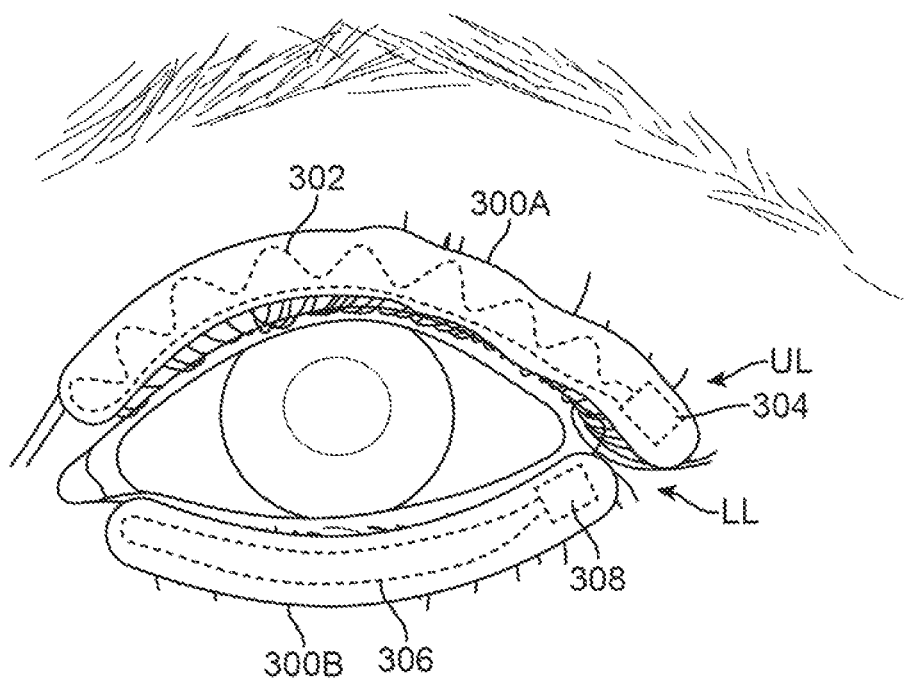
FIG. 36 shows yet another variation of treatment strips incorporating electrodes through the length of the strips.

Aside from the application of mechanical pressure or vibrational energy, other forms of energy may also be delivered by one or more of the treatment strips. Another variation is illustrated in FIG. 36 which shows an upper contoured strip 300A having a conductive element 302 such as a wire integrated along the entire length (or a partial length) of the contoured strip 300A. The conductive element 302 may be configured in an alternating pattern or it may be simply aligned along the length of the strip as shown by conductive element 306 (or electrically resistive) along the lower contoured strip 300B. Each of the conductive elements 302, 306 may be in electrical communication with a respective power supply and/or processor 304, 308. The conductive elements 302, 306 may be selectively actuated to apply either heat energy or they may configured to apply radio-frequency (RF) energy to the underlying skin and meibomian glands. With respect to the application of electrical energy, one form of electrical energy applicable by the treatment strips may include use of a transcutaneous electrical nerve stimulation feature, e.g., to deliver neural stimulation to increase tear production. The conductive elements may generate the thermal energy via various power sources, e.g., battery, solar cell, kinetic movement, RF, etc.

Figure 37:
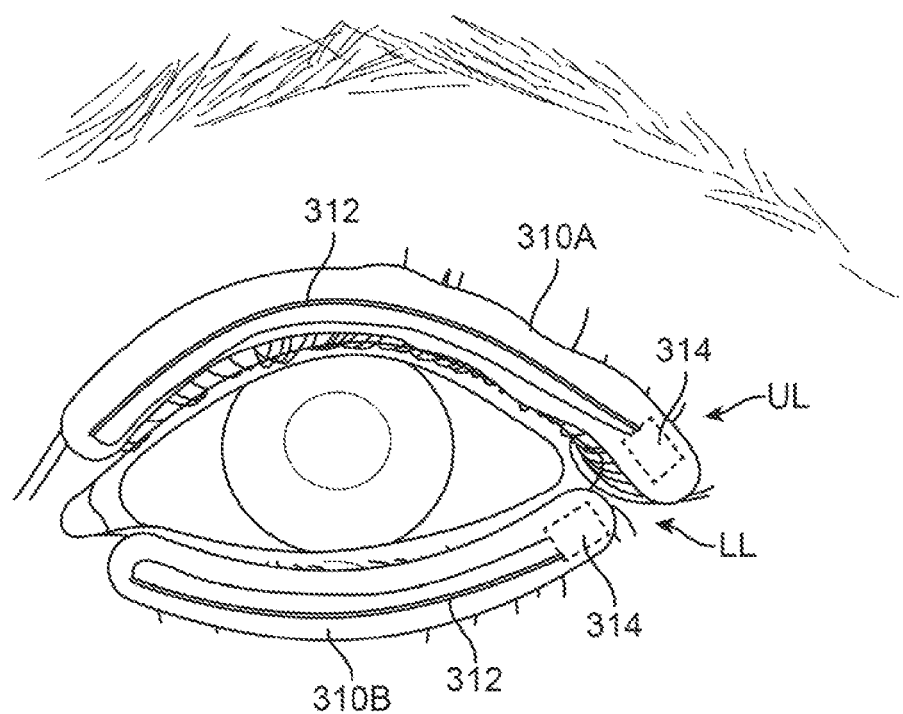
FIG. 37 shows yet another variation of treatment strips incorporating microwave antennas along the strips.
Figure 38:
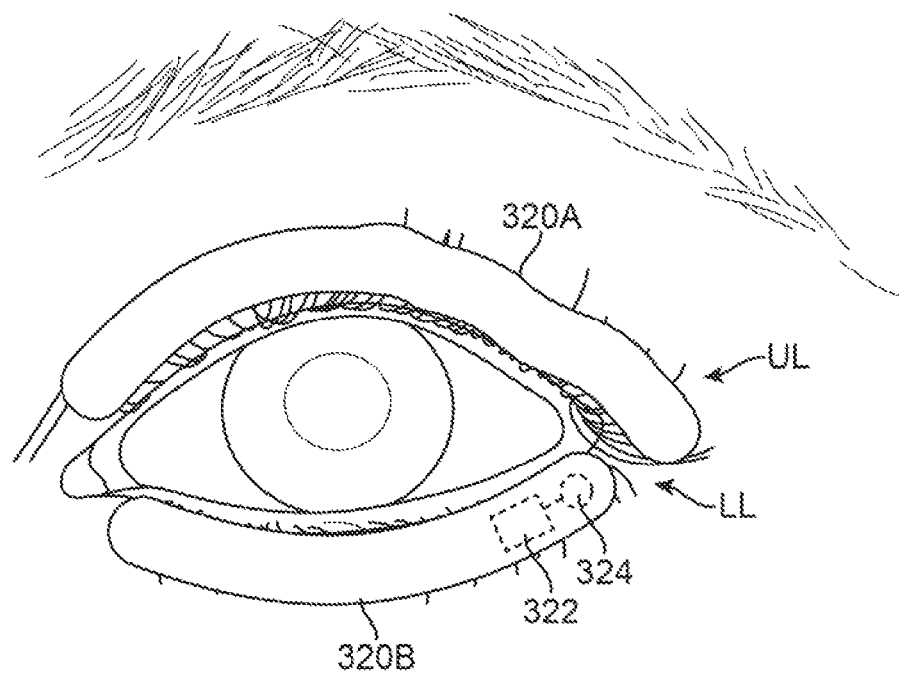
FIG. 38 shows yet another variation of a treatment strip incorporating a timer and indicating for alerting a user when a treatment has been completed.

FIG. 37 shows yet another variation where the contoured strips 310A, 310B may be configured to incorporate an electrode or antenna 312 coupled to a power supply and/or processor 314 for applying, e.g., microwave energy to the underlying meibomian glands. Aside from the electrical or microwave energy, the treatment strips may be configured to apply yet other forms of energy for treating the meibomian glands. For example, other variations may incorporate actuators or transmitters for applying ultrasonic, RF, microwave, magnetic, photonic (light energy in the infrared or visible light spectrum), etc. In yet other variations, the conductive elements may be configured to function as electromagnetic elements once actuated or the strips may incorporate ferromagnetic elements to promote closure of the eyelids. The magnetic force could serve to squeeze the meibomian glands and express the oily obstruction as the eyes are opened and re-opened when overcoming the magnetic force.

In yet another variation, one or both treatment strips 320A, 320B may be configured to incorporate an indicator 324, e.g., LED light, alarm, vibration element, etc., electrically coupled to a power supply and/or processor 322 to alert the patient when a prescribed treatment has been completed. This feature (and any of the other features) may be combined with any of the other variations of the treatment strips described herein as practicable.

Figure 39:
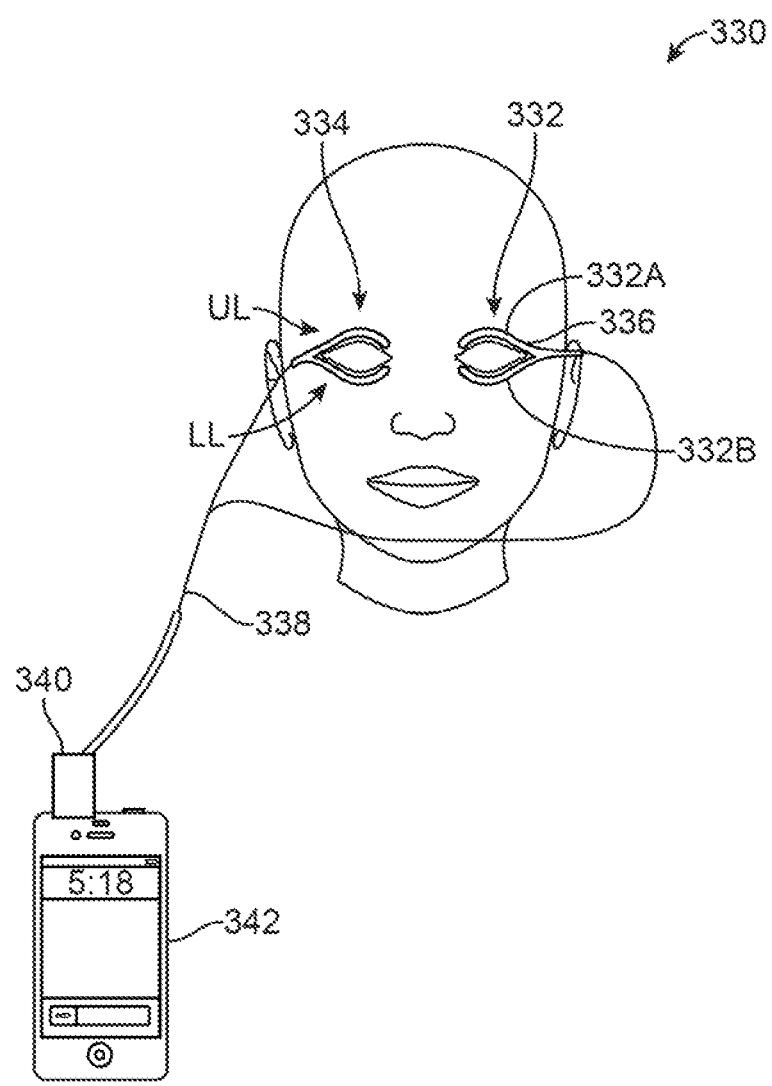
FIG. 39 shows yet another variation of an eyelid treatment system which may be coupled to a portable remote controller such as a smartphone or tablet.

FIG. 39 shows yet another variation where the eyelid treatment system 330 may be formed into a coupled dual-strip design, e.g., a "wishbone" design, where the dual-strip heating strips may have two heating elements which follow the location of the meibomian glands the upper UL and lower LL eyelid of a single eye. Depending upon whether both eyes or a single eye and/or both upper and lower eyelids are treated, the system 330 may comprise a first heating strip assembly 332 and a second heating strip assembly 334 for each respective eye. Each of the assemblies 332, 334 may accordingly utilize an upper and a lower lid treatment heater, e.g., upper lid treatment strip 332A and lower lid treatment strip 332B, where each of the upper and lower elements may be coupled to one another via wires 336. Moreover, each of the assemblies 332, 334 may be coupled via a connecting cable 338 to controller 340 which may be coupled (e.g., through an input/output port such as a headphone jack, USB port, or other connection port) to a portable electronic device 342 (e.g., smartphone having a touch screen interface, tablet, PDA, laptop computer, etc.) as shown.

In other variations, the number of connecting cables may range anywhere from 1-4 connector cables rather than utilizing a single cable 338. For instance, one cable may be used to provide power and communication to a few or all four heating elements in each of the assemblies 332, 334. Alternatively, four connecting cables may provide power and communication to each of the heating elements in assemblies 332, 334. Yet in other alternatives, two connecting cables may provide power and communication to each of the assemblies 332, 334.

In other additional variations, any of the treatment strips described may be used in combination with the controller 342 described herein, as practicable. Yet in a further variation, oval or circular shaped heating elements may covers the eye and both eyelids where an outer border of the heating elements or strips may follow the path of the upper and lower meibomian glands. In this case, one treatment strip may cover both eyelids and both sets of meibomian glands and the user may use a total of two (rather than four) round, circular, or oval shaped treatment strips to cover both eyes. Such a variation may be used, e.g., for a night time therapy in bed prior to or during sleep when the eyes need not necessarily be open.

The assemblies 332, 334 may generally comprise strips, as previously described, which follow the location of the meibomian glands while still allowing patients to blink easily and proceed in comfort with daily activity. An example of such heaters which may be configured for use with the treatment system 330 may include thin, flexible heaters which are commercially available through companies such as Minco Products, Inc. (Minneapolis, Minn.) or can be custom designed and manufactured independently or through third party manufacturing. Each individual treatment strip, e.g., treatment strips 332A, 332B, may each be sized for a single eyelid, e.g., 28 mm×7 mm×0.15 mm, having a bottom chord length of, e.g., 28 mm, with a radius of curvature of, e.g., 75 mm, and having a general configuration of an arcuate rectangle having blunted corners where the nasal or temporal edges may coincide with the radii of the arc. However, these size limitations are intended to be exemplary and not limiting since the treatment strips 332A, 332B may be sized to be smaller or larger to accommodate different eye anatomies.

Moreover, the individual treatment strips 332A, 332B may be formed as thin, flexible transparent polymers containing the heating elements while the contact surface of the strips may be affixed to the respective eyelids with, e.g., a disposable adhesive. Other variations may utilize opaque or colored strips, e.g., skin-tone colors. Moreover, one or more temperature sensors may also be integrated into the treatment strips where the heating elements and sensors may be routed through the connecting cable 338 to a power source and/or controller 340 and/or portable electronic device 342, as shown.

Controller 340 may generally comprise a hardware/software platform or unit which may be programmed for controlling the therapy treatments. Accordingly, the controller 340 may include a processor as well as a power supply such as a battery (rechargeable or disposable) for providing power to the assemblies 332, 334. The power supply within controller 340 may be optionally rechargeable separate from the portable electronic device 342 or the power supply may draw power for the assemblies 332, 334 and processor directly from the portable electronic device 342 as well.

In the case where the controller 340 is programmed to provide the therapy treatment protocols, one or several controls for controlling the treatments may be built directly into controller 340. The portable electronic device 342 may interface with the controller 340 to display, in one variation, part of the controls on a screen (e.g., touchscreen) of the electronic device 342 such as controls for starting and/or stopping a treatment. Alternatively, all of the controls may reside on the controller 340 while a display on the electronic device 342 may serve primarily to show or track various results or treatment parameters.

In yet another alternative, the all of the controls may reside on the display of the electronic device 342 for controlling the various treatment options and parameters rather than on the controller 340. In this variation, the electronic device 342, in this example a smartphone, may also provide the power to the treatment strip assemblies 332, 334 and may also control the various treatment temperatures and times as well as provide temperature feedback or other physiological parameters which may be measured. In this case, the treatment strips 332, 334 and connecting cable 338 may be plugged directly into the mobile or portable consumer electronic device 342. For instance, the electronic device 342 may be used to display treatment parameters and controls such as an icon or button for initiating therapy. In one example, therapy may be initiated by the user through electronic device 342 to heat one or more of the strips of one or both of the treatment strip assemblies 332, 334. In any of the variations, the electronic device 342, particularly in the case of a smartphone or tablet, may have an optional program or application downloaded onto the device which facilitates the various control and/or display parameters on the electronic device 342 depending upon how the electronic device 342 is used with the controller 340 and assemblies 332, 334.

Additionally, the electronic device 342 may also provide a diagnostic function to allow the user to test for dry eye and/or to determine how treatment is progressing either before, during, or after treatment. Accordingly, the electronic device 342 or controller 340 may leverage, e.g., an integrated camera and/or flash/light source, for purposes of imaging the user's ocular tear film or ocular surface and evaluating commonly used tear assessment criteria such as total tear film layer thickness, and/or tear film mucin layer thickness, and/or tear film lipid layer thickness, and/or tear film aqueous layer thickness, or any combination thereof. In addition to imaging of the user's tear film and/or ocular surface conditions, the mobile application may include other common methods for diagnosing dry eye such as user questionnaires related to the user patient's symptoms, discomfort, and/or improvement or worsening of symptoms that can be completed using the electronic device's touch screen interface, results stored on the electronic device 342 or web application or manufacturer's servers, tracked over time for trend evaluation, and possibly shared with the user's physician.

Moreover, in any of the variations, the controller 340 and/or electronic device 342 may be programmed or initiated to heat up the assemblies 332, 334 to, e.g., 42.5° C.+/−1° to 2° C. Treatment time may be set to, e.g., 15 to 30 minutes, and the controller 340 and/or electronic device 342 may further be programmed to shut down when the allotted treatment time has passed or if the measured temperature rises above a predetermined level, e.g., 45° C. Additionally, the controller 340 and/or electronic device 342 may also be programmed or set to indicate various treatment parameters (e.g., the initiation of treatment, warming of the heating elements, completion of treatment, errors, battery life, etc.) through any number of visual, auditory, or haptic indicators.

Additionally, the controller 340 and/or electronic device 342 may be used to store and/or transmit various data such as historical treatment data, usage time, total treatment time, temperature data, etc. Furthermore, the controller 340 and/or electronic device 342 may communicate wirelessly with a remote server or additional controller, allowing the controller 340 and/or electronic device 342 to also be programmed remotely, e.g., by a physician or other party. In yet other variations, audio and/or visual information (e.g., advertisements or other media) may also be displayed upon the controller 340 and/or electronic device 342 which may be received from remote servers or various other data may be transmitted to and/or from the controller 340 and/or electronic device 342 as well.

In yet other variations, although controller 340 is illustrated as being coupled to assemblies 332, 334 via a wired connecting cable 338, other variations may have controller 340 wirelessly connected with assemblies 332, 334. Such a connection may be through any number of wireless protocols such as Bluetooth®, RF, etc.

This "precision temperature control" mobile heating therapy system may be used for heating other parts of the body as well, where the system remains nearly the same, but the heating element dimensions may be varied and power requirements may also be changed depending on the total surface area being treated and temperature goals.

With the incorporation of a processor into the treatment strips, treatment times or other parameters such as temperature of the strips may be programmed and optionally shut on or off selectively by the patient or automatically. Moreover, other parameters such as the frequency of the heat delivery or other stimulation may also be programmed by the processor to provide further flexibility in treatment.

The applications of the devices and methods discussed above are not limited to the treatment of dry eye syndrome but may include any number of further treatment applications. Moreover, such devices and methods may be applied to other treatment sites within the body where acute or chronic inflammation causes a disease or condition. The treatment strips can be accordingly custom-designed to follow the path of the underlying physiology, e.g. custom designed and contoured cooling or heating treatment strips to treat the sinuses and acute or chronic sinusitis, respectively, rhinitis and allergic rhinitis, joint aches and inflammation, arthritis, muscle aches, back pain, headaches, wounds, sports injuries, etc. Modification of the above-described assemblies and methods for carrying out the invention, combinations between different variations as practicable, and variations of aspects of the invention that are obvious to those of skill in the art are intended to be within the scope of the claims.

What is claimed is:

1. A treatment system, comprising:
   an upper strip configured to adhere to an underlying region of skin of an upper eyelid of a subject such that the upper strip has a flexibility sufficient to accommodate movement of the upper eyelid to allow for the subject to blink naturally without restriction from the upper strip;
   a controller in communication with the upper strip via a connecting cable which transmits electrical energy to the upper strip, the controller being programmable for a treatment therapy,
   wherein the upper strip is configured to receive the electrical energy and emit thermal energy to the underlying region of skin, and
   wherein the upper strip has a first curved or arcuate periphery which is shaped to extend and follow a border of one or more meibomian glands contained within the underlying region of skin, and the upper strip further has a second curved or arcuate periphery which is shaped to extend and follow a free margin of the upper eyelid.

2. The system of claim 1 further comprising a lower strip configured to adhere to an underlying region of skin of a lower eyelid of the subject.

3. The system of claim 2 wherein the upper strip and lower strip are electrically coupled to one another.

4. The system of claim 2 wherein the upper strip and lower strip are electrically coupled to one another forming a wishbone design.

5. The system of claim 1 wherein the upper strip comprises a contact surface for placement against the region of skin.

6. The system of claim 1 wherein the upper strip comprises a heating layer in thermal communication with the region of skin.

7. The system of claim 6 further comprising a thermochromic layer in thermal communication with the heating layer.

8. The system of claim 1 wherein the controller is coupled to the connecting cable.

9. The system of claim 1 wherein the controller is programmed to control one or more parameters of the upper strip.

10. The system of claim 9 wherein the one or more parameters comprise a temperature, treatment time, frequency of treatment, or thermal profile of the upper strip.

11. The system of claim 9 wherein the controller is programmed to heat the upper strip to a temperature of between 40° to 50° C.

12. The system of claim 9 wherein the controller is programmed to heat the upper strip to a temperature up to 45° C.

13. The system of claim 9 wherein the controller is programmed to heat the upper strip to a temperature of between 40.5° to 44.5° C.

14. The system of claim 9 wherein the controller is programmed to heat the upper strip to a temperature of between 41.5° to 43.5° C.

15. The system of claim 1 further comprising one or more temperature sensors incorporated into the upper strip for regulating a temperature of the upper strip.

16. The system of claim 9 wherein the controller is programmed to heat the upper strip for at least 10 minutes or more.

17. The system of claim 9 wherein the controller is programmed to heat the upper strip for up to 15 minutes.

18. A method of treating a subject, comprising:
    adhering an upper strip to an upper eyelid of a subject such that the upper strip has a flexibility sufficient to accommodate movement of the upper eyelid to allow for the subject to blink naturally without restriction from the upper strip while covering one or more meibomian glands contained within the upper eyelid with the upper strip, wherein the upper strip has a first curved or arcuate periphery which is shaped to extend and follow a border of the one or more meibomian glands contained within the upper eyelid and a second curved or arcuate periphery which is shaped to extend and follow a free margin of the upper eyelid;
    initiating a treatment with the upper strip via a controller transmitting electrical energy to the upper strip via a connecting cable; and
    emitting thermal energy from the upper strip to the upper eyelid.

19. The method of claim 18 further comprising adhering a lower strip to a lower eyelid of the subject such that one or more meibomian glands contained within the lower eyelid are covered by the lower strip.

20. The method of claim 19 wherein the upper strip and lower strip are electrically coupled to one another.

21. The method of claim 18 wherein emitting thermal energy comprises applying thermal energy from a heating layer in the upper strip.

22. The method of claim 18 wherein initiating comprises programming the upper strip via the controller attached to the upper strip.

23. The method of claim 22 wherein programming comprises controlling one or more parameters of the upper strip.

24. The method of claim 23 wherein controlling comprises controlling a temperature, treatment time, frequency of treatment, or thermal profile of the upper strip.

25. The method of claim 18 wherein initiating further comprises displaying at least one parameter.

26. The method of claim 18 further comprising wirelessly communicating with a remote server.

27. The method of claim 18 wherein the method of treating comprises treating one or more conditions selected from the group consisting of dry eye, evaporative dry eye, and Meibomian gland dysfunction.

28. The method of claim 18 wherein the method of treating comprises treating to improve one or more conditions selected from the group consisting of an ocular surface, tear quality, lipid layer of tears, and tear break up time.

29. The method of claim 18 wherein the method of treating comprises treating to reduce Meibomian gland inflammation or ocular surface inflammation.

30. The method of claim 23 wherein controlling one or more parameters comprises heating the upper strip to a temperature of between 40° to 50° C.

31. The method of claim 23 wherein controlling one or more parameters comprises heating the upper strip to a temperature up to 45° C.

32. The method of claim 23 wherein controlling one or more parameters comprises heating the upper strip to a temperature of between 40.5° to 44.5° C.

33. The method of claim 23 wherein controlling one or more parameters comprises heating the upper strip to a temperature of between 41.5° to 43.5° C.

34. The method of claim 18 further comprising monitoring a temperature of the upper strip via one or more temperature sensors incorporated into the upper strip.

35. The method of claim 18 wherein emitting thermal energy comprises heating the upper strip for at least 10 minutes or more.

36. The method of claim 18 wherein emitting thermal energy comprises heating the upper strip for up to 15 minutes.

* * * * *